US012724034B2

(12) United States Patent
Yang et al.

(10) Patent No.: US 12,724,034 B2
(45) Date of Patent: Sep. 1, 2026

(54) TRYPTOPHAN OPTICAL PROBE, PREPARATION METHOD THEREFOR AND USE THEREOF

(71) Applicant: East China University of Science and Technology, Shanghai (CN)

(72) Inventors: Yi Yang, Shanghai (CN); Yuzheng Zhao, Shanghai (CN); Chenxia Zhang, Shanghai (CN); Li Huang, Shanghai (CN); Yejun Zou, Shanghai (CN); Xie Li, Shanghai (CN); Shuning Liu, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 1050 days.

(21) Appl. No.: 17/904,503

(22) PCT Filed: Feb. 9, 2021

(86) PCT No.: PCT/CN2021/076315
§ 371 (c)(1),
(2) Date: Mar. 3, 2023

(87) PCT Pub. No.: WO2021/164666
PCT Pub. Date: Aug. 26, 2021

(65) Prior Publication Data

US 2023/0296617 A1 Sep. 21, 2023

(30) Foreign Application Priority Data

Feb. 18, 2020 (CN) ......................... 202010099424.3

(51) Int. Cl.
*G01N 33/68* (2006.01)
*C12N 15/63* (2006.01)
*G01N 33/58* (2006.01)

(52) U.S. Cl.
CPC ......... *G01N 33/6812* (2013.01); *C12N 15/63* (2013.01); *G01N 33/582* (2013.01)

(58) Field of Classification Search
CPC .. G01N 33/6812; G01N 33/582; C12N 15/63; C12N 15/85; C12N 15/70; C07K 2319/60; C07K 14/3156; C09K 11/06; C09K 2211/10
See application file for complete search history.

(56) References Cited

U.S. PATENT DOCUMENTS 7,384,775 B2 * 6/2008 Zagursky ................. C12N 9/88 424/234.1
2008/0311047 A1 * 12/2008 Kaper .................. G01N 33/542 435/254.2

OTHER PUBLICATIONS

Chen et al., "Tryptophan Predicts the Risk for Future Type 2 Diabetes," PLoS One, Sep. 6, 2016, vol. 11, No. 9, p. e0162192.
Fontaine et al., "Near-Infrared Reflectance Spectroscopy (NIRS) Enables the Fast and Accurate Prediction of Essential Amino Acid Contents. 2. Results for Wheat, Barley, Corn, Triticale, Wheat Bran/Middlings, Rice Bran, and Sorghum," Journal of Agricultural and Food Chemistry, 2002, vol. 50, No. 14, pp. 3902-3911.
Friedman, Mendel, "Applications of the Ninhydrin Reaction for Analysis of Amino Acids, Peptides, and Proteins to Agricultural and Biomedical Sciences," Journal of Agricultural and Food Chemistry, 2004, vol. 52, No. 3, pp. 385-406.
GenBank Accession No. CVW92025.1 downloaded Nov. 27, 2023 (2 pages).
Nadler et al., "Rapid construction of metabolite biosensors using domain-insertion profiling," Nature Communications, 2016, vol. 7, p. 12266.
Sadok et al., "Chromatographic analysis of tryptophan metabolites," Journal of Separation Science, 2017, vol. 40, pp. 3020-3045.
Wu et al., "A rapid and specific colorimetric method for free tryptophan quantification," Talanta, 2018, vol. 176, pp. 604-609.
International Search Report and Written Opinion dated May 10, 2021 in corresponding International Patent Application No. PCT/CN2021/076315 (7 pages).
English translation of International Search Report and Written Opinion dated May 10, 2021 in corresponding International Patent Application No. PCT/CN2021/076315 (6 pages).

* cited by examiner

*Primary Examiner* — Shafiqul Haq
(74) *Attorney, Agent, or Firm* — Greenberg Traurig, LLP; Melissa Hunter-Ensor; Nathan Hsu

(57) ABSTRACT

Disclosed is a tryptophan optical probe, a preparation method therefor and the use thereof. Disclosed is an optical probe, comprising a tryptophan-sensitive polypeptide or a functional variant thereof and an optically active polypeptide or a functional variant thereof, wherein the optically active polypeptide or the functional variant thereof is located in the sequence of the tryptophan-sensitive polypeptide or the functional variant thereof. Furthermore, disclosed are a method for preparing the above-mentioned probe and the use thereof in the detection of tryptophan.

9 Claims, 16 Drawing Sheets

Specification includes a Sequence Listing.

A

B

C

TRYPTOPHAN OPTICAL PROBE, PREPARATION METHOD THEREFOR AND USE THEREOF

TECHNICAL FIELD

The present invention relates to the field of optical sensor technology, especially to a tryptophan optical sensor, preparation method thereof and application thereof.

CROSS-REFERENCE TO RELATED APPLICATION

This application is a U.S. National Stage Application, pursuant to 35 U.S.C. § 371, of PCT International Application No. PCT/CN2021/076315, filed Feb. 9, 2021, which claims priority to and the benefit of Chinese Patent Application No. 202010099424.3, filed Feb. 18, 2020, the entire contents of each of which are incorporated herein by reference in their entirety.

SEQUENCE LISTING

This application contains a Sequence Listing which has been submitted electronically in ASCII format and is hereby incorporated by reference in its entirety. Said ASCII copy, created on Jan. 26, 2023, is named 197277 seq_EN.txt, and is 173,193 bytes in size.

BACKGROUND ART

L-tryptophan is one of the essential amino acids indispensable for human growth and development. Among the 20 amino acids that make up protein, tryptophan accounts for the smallest proportion in protein and cytoplasm. In addition to regulating protein synthesis, it and its metabolites also participate in many physiological functions, which is important for the development and function of many organs in the body.

The metabolism of tryptophan in different tissues is related to various physiological functions. The kynurenine pathway is the main pathway of tryptophan metabolism in humans and mammals, and most of it occurs in the liver. In this pathway, tryptophan generates N-formylkynurenine and kynurenine under the action of tryptophan 2.3-dioxygenase (TDO) (mainly in the liver) or indoleamine 2.3-dioxygenase (IDO) (widely presenting in many tissues). After that, active molecules such as quinolinic acid, niacin, kynurenic acid and xanthuric acid are generated through multi-stage enzymatic reaction. Kynurenine is a non-selective N-methyl-D-aspartate (NMDA) receptor blocker that inhibits excitation of the nervous system. Quinolinic acid is related to gluconeogenesis and can also bind to NMDA receptors to excite neurotransmitters. Niacin is a precursor for the synthesis of coenzyme I (nicotinamide adenine dinucleotide, NAD) and coenzyme II (nicotinamide adenine dinucleotide phosphate, NADP), and acts as a hydrogen transfer body in biological oxidation. In the gut and brain, tryptophan is catalyzed by tryptophan hydroxylase (TPH) to synthesize 5-HTP (5-hydroxytryptophan), which is then converted to 5-HT (5-hydroxytryptamine) by decarboxylase, which is another important way of tryptophan metabolism in the body. Serotonin (5-HT) is a brain neurotransmitter, platelet clotting factor and neurohormone found throughout organs throughout the body. It also causes blood vessels to narrow, and changes in serotonin levels in the brain can alter mood. In the pineal gland, the further conversion of serotonin to melatonin has a pronounced circadian rhythm, which regulates sleep and wakefulness, and is also involved in anti-oxidative stress and immune regulation.

Research has found that there are many conditions or diseases characterized by tryptophan deficiency. For example, fructose malabsorption can lead to improper absorption of tryptophan in the gut, which can reduce the amount of tryptophan in the blood and lead to depression. A diet high in corn or other tryptophan deficiency can lead to pellagra, a niacin-tryptophan deficiency with symptoms of dermatitis, diarrhea, and dementia. Hartnup disease is a disorder in which tryptophan and other amino acids are not absorbed properly, and symptoms include a rash, difficulty coordinating movements (cerebellar ataxia), and psychiatric symptoms such as depression or psychosis. In some cases, tryptophan can also be a neurotoxin and endotoxin, causing adverse health effects at chronically high levels. Long-term high levels of tryptophan as found in type I glutaric aciduria, the body cannot fully break down lysine, hydroxylysine, and chromophore due to a deficiency of mitochondrial glutaryl-CoA dehydrogenase (GCDH), and excess intermediate breakdown products build up and cause damage to the brain as well as other organs. High levels of tryptophan have also been linked to eosinophilia-myalgia syndrome (EMS), an incurable and sometimes fatal flu-like neurological disorder. All in all, the accurate and timely determination of tryptophan concentration or concentration change trend under physiological conditions can not only be used to evaluate nutritional status, but also has important value for clinical diagnosis of various diseases and subsequent targeted treatment monitoring.

At present, the most commonly used methods for detecting tryptophan are HPLC (Sadok, I. et al. J Sep Sci 2017, 40, (15), 3020-3045), high performance capillary electrophoresis, mass spectrometry (Chen, T. et al. PLoS One 2016, 11, (9), e0162192), chromatography, UV absorption, visible photometry (Friedman, M. J Agric Food Chem 2004, 52, (3), 385-406; Wu, Y. et al. Talanta 2018, 176, 604-609), near-infrared reflectance spectroscopy (Fontaine, J. et al. J Agric Food Chem 2002, 50, (14), 3902-11), fluorescence spectroscopy, flow injection assay, ELISA, etc. These detection and analysis methods may require professional analytical instruments and equipment, or the steps are cumbersome and prone to human error, and are only suitable for in vitro detection, and cannot monitor the change of tryptophan concentration in living cells in real time. Therefore, there is an urgent need to develop new detection methods to achieve simple, rapid, and high-specificity real-time, localization, quantitative, and high-throughput detection of tryptophan in and out of cells.

SUMMARY OF INVENTION

The purpose of the present invention is to provide sensors and methods for real-time localization, high-throughput, and quantitative detection of tryptophan in and out of cells.

To achieve the above object, the invention provides the following technical solutions:

The present invention provides a tryptophan optical sensor (probe), comprising a tryptophan-sensitive polypeptide and an optically active polypeptide, wherein the optically active polypeptide is located within the sequence of the tryptophan-sensitive polypeptide. The tryptophan-sensitive polypeptide is divided into a first part and a second part by an optically active polypeptide or a functional variant thereof.

The invention provides a tryptophan optical sensor comprising tryptophan-sensitive polypeptide B and optically active polypeptide A, wherein the optically active polypeptide A is located in the sequence of the tryptophan-sensitive polypeptide B, dividing the tryptophan-sensitive polypeptide B into the first part B1 and the second part B2, forming a sensor structure of type B1-A-B2.

In one embodiment, the tryptophan-sensitive polypeptide is a tryptophan-binding protein or a functional fragment thereof. In one embodiment, the tryptophan-sensitive polypeptide is derived from Streptococcus pneumoniae. In one embodiment, the tryptophan-sensitive polypeptide is tryptophan-binding protein 31ft. In one embodiment, the tryptophan-sensitive polypeptide has the sequence shown in SEQ ID NO: 1 or a fragment thereof, or the sequence having at least 35%, at least 40%, at least 50%, at least 60%, at least 70%, at least 80%, at least 85%, at least 90%, at least 95%, at least 97%, at least 99% sequence identity with SEQ ID NO: 1 and retains tryptophan-binding function.

In one embodiment, the optically active polypeptide is a fluorescent protein or a functional variant thereof. In one embodiment, the fluorescent protein is selected from the group consisting of yellow fluorescent protein (cpYFP as shown in SEQ ID No: 2), orange fluorescent protein, red fluorescent protein, green fluorescent protein (cpGFP as shown in SEQ ID No: 3), blue fluorescent protein (cpBFP as shown in SEQ ID No: 4), and apple red fluorescent protein (cpmApple as shown in SEQ ID No: 5). Preferably, the optically active polypeptide is cpYFP. In one embodiment, the fluorescent protein has a sequence as shown in any of SEQ ID NO: 2-5.

In one embodiment, the optical sensor further comprises one or more linkers flanking the optically active polypeptide. The linker of the present invention can be any amino acid sequence of any length. In one embodiment, the optically active polypeptide is flanked by a linker of no more than 5 amino acids, such as a linker of 0, 1, 2, 3, 4 amino acids. In one embodiment, the linker flanking the optically active polypeptide comprises amino acid Y. In one embodiment, linker Y is located N-terminal and/or C-terminal to the optically active polypeptide. In one embodiment, the optical sensor is shown as follows: the first part of the tryptophan-sensitive polypeptide B1-Y-optically active polypeptide A-the second part B2 of the tryptophan-sensitive polypeptide. In one embodiment, the present optical sensor does not comprise a linker.

The optically active polypeptide of the present invention can be located at any position of the tryptophan-sensitive polypeptide. In one embodiment, the optically active polypeptide is located in one or more positions of the tryptophan-sensitive polypeptide selected from the group consisting of residues 114-118, 233-235 and/or 263-268, the numbering corresponding to the full length of the tryptophan binding protein. In one embodiment, the optically active polypeptide replaces one or more amino acids of the tryptophan-sensitive polypeptide at one or more positions selected from: residues 114-118, 233-235 and/or 263-268, the numbering corresponding to the full length of tryptophan-binding protein.

In one embodiment, the optically active polypeptide is located in the tryptophan-sensitive polypeptide at one or more positions selected from the group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 and/or 267/268. Preferably, the optically active polypeptide is located at one or more positions of the tryptophan-sensitive polypeptide selected from the group consisting of 263/265, 263/266, 263/267 and 263/268.

In an exemplary embodiment, the optical sensor of formula B1-A-B2 of the present invention may be a sensor with cpYFP inserted in one or more sites of the tryptophan-binding protein selected from the group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 and/or 267/268. In an exemplary embodiment, the optical sensor of formula B1-A-B2 of the present invention may be a sensor with a cpYFP inserted in one or more sites of the tryptophan-binding protein selected from the following group consisting of: 114/115, 114/116, 114/118, 115/118, 116/118, 117/118, 233/235, 263/265, 263/266, 263/267, 263/268, 264/265, 264/266, 264/267, 265/266, 266/267 or 266/268. Preferably, the optical sensor of the present invention may be a sensor with a cpYFP inserted in one or more sites of the tryptophan binding protein selected from the following group consisting of 263/265, 263/266, 263/267 and 263/268.

In one or more embodiments, the optical sensor of the present invention may be a sensor with a cpGFP inserted in one or more sites of the tryptophan binding protein selected from the following group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 or 267/268. In one or more embodiments, the optical sensor of the present invention may be a sensor with a cpGFP inserted in one or more sites of the tryptophan binding protein selected from the group consisting of: 114/117, 114/118, 115/117, 116/117, 116/118, 117/118, 233/234, 263/264, 263/265, 263/266, 263/267, 263/268, 264/265, 264/266, 264/267, 265/267 or 266/267. In a preferred embodiment, the optical sensor of the present invention may be a sensor with a cpGFP inserted in one or more sites of the tryptophan binding protein selected from the following group consisting of: 263/265, 263/266, 263/267 and 263/268.

In one or more embodiments, the optical sensor of the present invention may be a sensor with cpBFP inserted in one or more sites of the tryptophan binding protein selected from the following group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 or 267/268. In one or more embodiments, the optical sensor of the present invention may be a sensor with a cpBFP inserted in one or more sites of a tryptophan binding protein selected from the following group consisting of: 114/115, 114/117, 114/118, 115/118, 116/118, 233/235, 263/265, 263/266, 263/267, 263/268, 264/265, 264/266, 265/266, or 266/267. In a preferred embodiment, the optical sensor of the present invention may be a sensor with a cpBFP inserted in one or more sites of the tryptophan binding protein selected from the following group consisting of: 263/265, 263/266, 263/267 and 263/268.

In one or more embodiments, the optical sensor of the present invention may be a sensor with a cpmApple inserted in one or more sites of the tryptophan binding protein selected from the group consisting of: 114/115, 114/116, 114/117, 114/118, 115/116, 115/117, 115/118, 116/117, 116/118, 117/118, 233/234, 233/235, 234/235, 263/264, 263/

265, 263/266, 263/267, 263/268, 264/265, 264/266, 264/267, 264/268, 265/266, 265/267, 265/268, 266/267, 266/268 or 267/268. In one or more embodiments, the optical sensor of the present invention may be a sensor with a cpmApple inserted in one or more sites of a tryptophan binding protein selected from the group consisting of: 114/115, 117/118, 263/264, 263/265, 263/266, 263/267, 264/268 or 265/266. In a preferred embodiment, the optical sensor of the present invention may be a sensor with a cpmApple inserted in one or more sites of the tryptophan binding protein selected from the group consisting of 263/264, 263/265, 263/266.

In one embodiment, the optical sensors of the present invention have or consist of the sequences shown in SEQ ID NO: 6-9.

The present invention also provides mutants of tryptophan-sensitive polypeptides. The amino acid mutation includes amino acid modification, substitution, deletion or sequence truncation. In one or more embodiments, the mutation is at 1, 2, 3, 4, 5, 6 or more sites of H13, T71, L84, D93, K105, N117, T130, V170, V192, F202, K214, Y217, K255, T259, 1283 of tryptophan binding protein. Exemplarily, the mutation is selected from 1, 2, 3, 4, 5, 6 or more of the following: H13F, H13W, T71F, T71W, L84F, L84W, D93F, D93W, K105F, K105W, N117F, N117W, T130F, T130W, V170F, V170W, V192F, V192W, F202W, K214F, K214W, Y217F, Y217W, K255F, K255W, T259F, T259W, I283F and/or I283W.

The present invention also provides optical sensors comprising tryptophan-sensitive polypeptides with one or more mutations. In one or more embodiments, the optical sensor is any optical sensor inserted with an optically active polypeptide as described above, and the tryptophan-sensitive polypeptide in the optical sensor has mutations at 1, 2, 3, 4, 5, 6 or more sites selected from H13, T71, L84, D93, K105, N117, T130, V170, V192, F202, K214, Y217, K255, T259, 1283. In one or more embodiments, an optical sensor comprising a mutated tryptophan-sensitive polypeptide is no less responsive to tryptophan than its unmutated counterpart. Preferably, the mutation is selected from 1, 2, 3, 4, 5, 6 or more of the following: H13F, L84F, L84W, D93F, D93W, K105F, K105W, N117F, N117W, V170F, V170W, V192F, F202W, K214F, K214W, Y217F, Y217W, K255F, K255W, T259F, T259W, I283F and I283W.

In an exemplary embodiment, the optical sensor of the present invention may be a fusion polypeptides of tryptophan binding protein having a fluorescent protein inserted at one or more sites selected from the group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 or 267/268 and having one or more mutations selected from the group consisting of: H13F, L84F, L84W, D93F, D93W, K105F, K105W, N117F, N117W, V170F, V170W, V192F, F202W, K214F, K214W, Y217F, Y217W, K255F, K255W, T259F, T259W, I283F and I283W. Preferably, the optical sensor of the present invention is a fusion polypeptides of tryptophan binding protein with a cpYFP inserted in one or more sites selected from 263/265, 263/266 or 263/267 and having one or more mutations selected from the group consisting of: L84F, K105F, K105W, N117F, V170F, F202W, K214F, K214W, Y217F, Y217W, K255F, K255W, T259F, T259W, I283F or I283W. In an exemplary embodiment, the tryptophan binding protein is SEQ ID NO: 1. Preferably, the optical sensors of the present invention have or consist of the sequences shown in SEQ ID NO: 10-39.

The optical sensors of the present invention comprise any of the amino acid sequence of SEQ ID NO: 6-39 or a variant thereof. In one embodiment, the optical sensors of the present invention comprise sequences having at least 35%, at least 40%, at least 50%, at least 60%, at least 70%, at least 80%, at least 85%, at least 90%, at least 95%, at least 99% sequence identity with any one of the amino acid sequences of SEQ ID NO: 6-39 retains the function of detecting tryphophan. In a preferred embodiment, the optical sensor provided by the present invention comprises a sequence substantially similar or identical to any of the amino acid sequences SEQ ID NO: 6-39. In a more preferred embodiment, the optical sensor provided by the present invention comprises or consists of any one of SEQ ID NO: 10-39.

The invention also provides fusion polypeptides comprising the optical sensors described herein and other polypeptides. In some embodiments, other polypeptides are located N- and/or C-terminal to the said optical sensor. In some embodiments, other polypeptides include polypeptides that localize optical sensors to different organelles or subcellular organelles, tags for purification, or tags for immunoblotting.

The invention also provides nucleic acid sequences encoding the polypeptides, sensors or proteins described herein, or complements or fragments thereof. In one embodiment, the nucleic acid sequence of the present invention is selected from (1) the coding sequence of the amino acid sequence shown in any of SEQ ID NOs: 6-39 or its complement, (2) and (1) having at least 99%, Sequences that are at least 95%, at least 90%, at least 80%, at least 70% or at least 50% identical, fragments of (3) (1) or (2). In one or more embodiments, the fragments are primers. In one embodiment, the nucleic acid sequence of the present invention comprises the nucleotide sequence of SEQ ID NO: 40 or a variant thereof, the amino acid sequence encoded by the variant having the function of detecting tryptophan. In a preferred embodiment, the present invention provides a nucleic acid sequence comprising at least 99%, at least 95%, at least 90%, at least 80%, at least 70% or at least 50% identical to the nucleotide sequence of SEQ ID NO: 40. In another preferred embodiment, the present invention provides a nucleic acid sequence comprising a nucleotide sequence substantially similar or identical to the nucleotide sequence of SEQ ID NO: 40.

The present invention also relates to complementary sequences of the above nucleic acid sequences or variants thereof, which may comprise nucleic acid sequences or complementary sequences thereof encoding fragments, analogs, derivatives, soluble fragments and variants of the optical sensors or fusion polypeptides of the present invention.

The invention also provides nucleic acid constructs comprising the nucleic acid sequences described herein, or their complementary sequences, which encode the optical sensors or fusion polypeptides described herein. In one or more embodiments, the nucleic acid construct is a cloning vector, expression vector, or recombinant vector. In one or more embodiments, the nucleic acid sequence is operably linked to an expression control sequence. In some embodiments, the expression vector is selected from the group consisting of prokaryotic expression vector, eukaryotic expression vector, and viral vector.

The invention also provides cells comprising the nucleic acid sequences or nucleic acid constructs of the invention. In one or more embodiments, the cells express an optical sensor or fusion polypeptide described herein.

The present invention also provides a detection kit comprising a tryptophan optical sensor or fusion polypeptide described herein or a tryptophan optical sensor or fusion polypeptide prepared as described herein.

The invention provides methods for preparing the optical sensors described herein, comprising providing cells expressing the optical sensors or fusion polypeptides described herein, culturing the cells under conditions in which the cells express them, and isolating the optical sensors or fusion polypeptides. In one embodiment, the method of preparing the tryptophan optical sensor or fusion polypeptide described herein comprises: 1) transferring an expression vector encoding a tryptophan optical sensor described herein into a host cell; 2) culturing the host cell under conditions suitable for the expression of the expression vector, and 3) isolating the tryptophan optical sensor.

The invention also provides a method for detecting tryptophan in a sample, comprising contacting the sample with an optical sensor or fusion polypeptide described herein, or an optical sensor or fusion polypeptide prepared according to the method described herein, and detecting changes in an optically active polypeptide. The detecting may be performed in vivo, in vitro, subcellularly, or in situ. Said sample is such as blood.

The invention also provides a method for quantitating tryptophan in a sample, comprising contacting the sample with an optical sensor or fusion polypeptide described herein or an optical sensor or fusion polypeptide prepared according to the method described herein, detecting changes in optically active polypeptide, and quantitating tryptophan in the sample according to the changes in optically active polypeptide.

The invention also provides a method for screening compounds, such as pharmaceuticals, comprising contacting a candidate compound with an optical sensor or fusion polypeptide described herein, or an optical sensor or fusion polypeptide prepared as described herein, detecting changes in the optically active polypeptide, and screening the compounds according to the changes in the optically active polypeptide. Said method allows high-throughput screening of compounds.

The invention also provides use of a tryptophan optical sensor or fusion polypeptide described herein or a tryptophan optical sensor or fusion polypeptide prepared according to the methods described herein in intracellular/extracellular localization of tryptophan. In one or more embodiments, the localization is in real time.

Beneficial effects of the present invention: The tryptophan optical sensor provided by the invention is easy to mature, has large dynamic change of fluorescence and good specificity and it can be expressed in cells through the method of gene manipulation, and it can locate, high-throughput, and quantitatively detect tryptophan in and out of cells in real time, eliminating the time-consuming steps of sample processing. The experimental results show that the highest response of the tryptophan optical sensor provided in this application to tryptophan is more than 9-fold increase of the control, and it can locate, qualitatively and quantitatively detect cells in subcellular structures such as cytoplasm, mitochondria, nucleus, endoplasmic reticulum, lysosome and Golgi apparatus, and can perform high-throughput compound screening and quantitative detection of tryptophan in blood.

BRIEF DESCRIPTION OF THE DRAWINGS

The invention is further illustrated below in combination with the drawings and examples.

DETAILED DESCRIPTION

Figure 1:
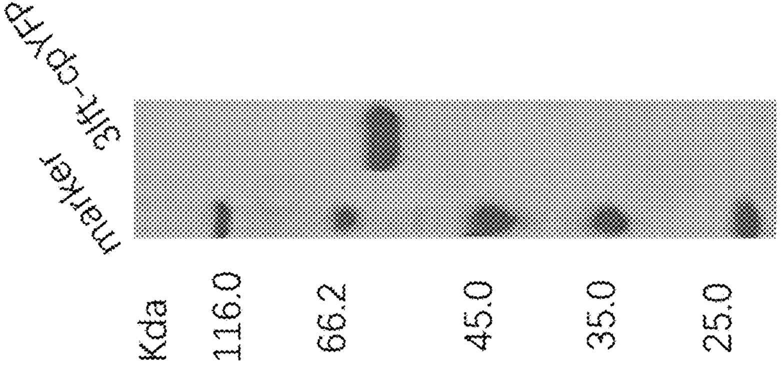
FIG. 1 is an SDS-PAGE graph of the exemplary tryptophan optical sensor described in Example 1.

When a value or range is given, the term "about" used herein means that the value or range is within 20%, within 10%, and within 5% of the given value or range.

The term "tryptophan-sensitive polypeptide" or "tryptophan-responsive polypeptide" used herein refers to a polypeptide which responds to tryptophan production including any response in chemical, biological, electrical, or physiological parameters of a polypeptide that interacts with the sensitive-polypeptide. The response includes small changes, for example, changes in the orientation of the amino acid or peptide fragment of the polypeptide and, for example, changes in the primary, secondary or tertiary structure of the polypeptide, including, for example, changes in protonation, electrochemical potential and/or conformation. "Conformation" is the three-dimensional arrangement of the primary, secondary, and tertiary structure of a molecule containing side groups in the molecule; when the three-dimensional structure of the molecule changes, the conformation changes. Examples of conformational changes include transitions from α-helix to β-fold or from β-fold to α-helix. It should be understood that detectable alterations need not be conformational changes as long as the fluorescence of the fluorescent protein moiety is altered. The tryptophan-sensitive polypeptide described herein may also include functional variants thereof. The functional variants of the tryptophan-sensitive polypeptide include, but are not limited to, variants that can interact with tryptophan and thereby undergo the same or similar changes as the parent tryptophan-sensitive polypeptide.

The tryptophan-sensitive polypeptides of the present invention include, but are not limited to, tryptophan-binding protein 31ft or variants with more than 90% homology thereto. The exemplary tryptophan binding protein 31ft of the present invention is derived from *Streptococcus pneumoniae.* 31ft is a family of ABC transporters consisting of two domains connected by three flexible amino acid peptide chains. Tryptophan-binding proteins can sense changes in tryptophan concentration, and the spatial conformation of tryptophan-binding proteins also changes greatly during the dynamic change of tryptophan concentration. An exemplary 31ft protein is shown in SEQ ID NO:1. In one or more embodiments, the tryptophan-sensitive polypeptide comprises the tryptophan-binding domain of the protein and does not include the DNA-binding domain. When describing an optical sensor or tryptophan-binding protein of the invention (eg., when describing an insertion site or a mutation site), references to amino acid residue numbering refer to SEQ ID NO: 1.

The term "optical sensor" as used herein refers to an tryptophan-sensitive polypeptide fused to an optically active polypeptide. The inventors discovered that the conformational changes produced by binding an tryptophan-sensitive polypeptide, such as an tryptophan binding protein to a physiological concentration of tryptophan specifically by tryptophan sensitive polypeptides causes conformational changes in an optically active polypeptides, such as fluorescent proteins, which in turn result in the alteration of the optical properties of the optically active polypeptides. A standard curve is plotted with the help of the fluorescence of fluorescent proteins determined at different concentrations of tryptophan allows the presence and/or level of tryptophan to be detected and analyzed.

In the present optical sensor, an optically active polypeptide, such as a fluorescent protein, is operably inserted into a tryptophan-sensitive polypeptide. The protein-based "optically active polypeptides" are polypeptides with the ability to emit fluorescence. In the present optical sensor, an optically active polypeptide, such as a fluorescent protein, is operably inserted into a tryptophan-sensitive polypeptide. Preferably, the protein substrate is selected to have fluorescence properties that are easily distinguishable in the unactivated and activated conformational states. The optically active polypeptide described herein may also include a functional variant thereof. A functional variant of the optically active polypeptide includes, but is not limited to, a variant for which the same or similar change in fluorescence property may occur as the parent optically active polypeptide.

The term "fluorescent protein" used herein refers to a protein that fluoresces upon irradiation with excitation light. Fluorescent proteins have been used as basic detection means in the field of biological sciences, such as green fluorescent protein (GFP) commonly used in biotechnology and circularly rearranged blue fluorescent protein (cpBFP), circularly rearranged green fluorescent protein (cpGFP), circularly rearranged yellow fluorescent protein (cpYFP) derived from mutations in this protein, etc; there are also a red fluorescent protein (RFP) commonly used in the art, and circularly rearranged proteins derived from this protein, such as cpmApple, cpmOrange, cpmKate, and others. Those skilled in the art know fluorescent proteins and sequences thereof that can be used for the invention. Exemplarily, cpYFP as shown in SEQ ID No: 2; cpGFP as shown in SEQ ID No: 3; cpBFP as shown in SEQ ID No: 4; and cpmApple as shown in SEQ ID No: 5.

A "linker" or "linker region" refers to an amino acid or nucleotide sequence linking two parts in a polypeptide, protein, or nucleic acid of the invention.

Exemplarily, the number of amino acids at the amino terminus of the linker region of the tryptophan-sensitive polypeptide to the optically active polypeptide in the invention is selected to be 0-3, and the number of amino acids at the carboxyl terminus is selected to be 0-2; when a recombinant optical sensor is linked to a functional protein as a basic unit, it can be fused at the amino or carboxyl terminus of the recombinant optical sensor. The linker sequence may be a short peptide chain composed of one or more flexible amino acids, as in Y.

The tryptophan optical sensors of the invention include tryptophan-sensitive polypeptide (B), such as a tryptophan binding protein or its variants, and optically active polypeptide (A), such as a fluorescent protein. The optically active polypeptide (A) is inserted into the tryptophan sensitive polypeptide (B), and B was divided into two parts, B1 and B2, to form the sensor structure of the formula B1-A-B2; the interaction between the tryptophan-sensitive polypeptide B and tryptophan results in a stronger optical signal for optically active polypeptide (A).

In the present optical sensor, the optically active polypeptide may be located anywhere in the tryptophan-sensitive polypeptide. In one embodiment, the optically active polypeptide is located anywhere in N-C direction over a tryptophan-sensitive polypeptide in N-C direction. Specifically, the optically active polypeptide is located in a flexible region of a tryptophan-sensitive polypeptide that refers to some specific structures present in higher structures of a protein such as loop domains, which are more mobile and flexible than other higher structures of the protein, and this region may undergo dynamic changes in spatial structural conformation upon binding of this protein and a ligand. The flexible region mentioned in the present invention mainly refers to the region where the insertion site is located in the tryptophan-binding protein, such as the regions of amino acid residues 114-118, 233-235 and/or 263-268. Illustratively, the optically active polypeptide is located at one or more positions of the tryptophan-sensitive polypeptide selected from the group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 and/or 267/268. Preferably, the optically active polypeptide is located at one or more positions of the tryptophan-sensitive polypeptide selected from the group consisting of 263/265, 263/266, 263/267 and 263/268. In the present invention, if the two numbers in a site represented in "X/Y" form are consecutive integers, this means that the optically active polypeptide is located between the amino acids stated by those numbers. For example, insertion site 114/115 indicates that the optically active polypeptide is located between amino acids 114 and 115 of the tryptophan-sensitive polypeptide. If the two numbers in a site represented in "X/Y" form are not consecutive integers, it indicates that the optically active polypeptide displaces the amino acids between the amino acids indicated by those numbers. For example, insertion site 114/116 indicates the replacement of amino acid 115 of the tryptophan-sensitive polypeptide by an optically active polypeptide.

When referring to a certain polypeptide or protein, the term "variant" or "mutant" used herein includes variants that have the same function of said polypeptide or protein but differ in sequence. Variants of polypeptides or proteins can include: homologous sequences, conservative variants, allelic variants, natural mutants, induced mutants. These variants include, but are not limited to: deletions, insertions and/or substitutions of one or more (usually 1-30, preferably 1-20, more preferably 1-10, most preferably 1-5) amino acids in the sequence of the polypeptide or protein, and sequences obtained by adding one or more (usually within 20, preferably within 10, more preferably within 5) amino acids to its carboxy terminus and/or amino terminus. These variants may also comprise at least about 70%, at least about 75%, at least about 80%, at least about 85%, at least about 90%, at least about 95%, at least about 98%, at least about 99% or 100% sequence identity to the polypeptide or protein. Not limited by theory, an amino acid residue is altered without changing the overall configuration and function of the polypeptide or protein, i.e., a functionally conserved mutation. For example, in the art, substitution with amino acids of approaching or similar perperty generally does not alter the function of a polypeptide or protein. In the art, amino acids with similar property tend to refer to families of amino acids with similar side chains, which have been well defined in the art. These families include amino acids with basic side chain (e.g., lysine, arginine, histidine), amino acids with acidic side chain (e.g., aspartic acid, glutamic acid), amino acids with uncharged polar side chain (e.g., glycine, asparagine, glutamine, serine, threonine, tyrosine, cysteine), amino acids with non-polar side chain (e.g., alanine, valine, leucine, isoleucine, tryptophan, phenylalanine, methionine, tryptophan), amino acids with β-branched side chain (e.g., threonine, valine, isoleucine) and amino acids with aromatic side chain (e.g., tyrosine, phenylalanine, tryptophan, histidine). For another example, the addition of one or more amino acids to the amino terminus and/or carboxy terminus also generally does not alter the function of a polypeptide or protein. The conservative amino acid substitutions of many commonly known non-genetic coding amino acids are known in the art. Conservative substitutions of other non-coding amino acids can be determined based on a comparison of their physical properties with those of the amino acids that are genetically encoded.

In two or more sequences of a polypeptide or nucleic acid molecule, the terms "identity" or "percent identity" refer to when the maximum correspondence is compared and aligned by manual alignment and visual inspection using methods known in the art such as sequence comparison algorithms, in a comparison window or a specified region, two or more sequences or subsequences are identical or have a certain percentage of amino acid residues or nucleotides that are identical in the specified region (e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical). For example, the preferred algorithms suitable for determination of percent identity and percent similarity are the BLAST and BLAST 2.0 algorithms, respectively, see Altschul et al., (1977) nucleic acids res. 25:3389 and Altschul et al., (1990) J. mol. Biol 215:403.

Those skilled in the art is well known that in gene cloning operation, it is often necessary to design a suitable restriction enzyme cutting site, which is bound to introduce one or more incoherent residues at the ends of the expressed polypeptide or protein, and this does not affect the activity of the polypeptide or protein of interest. Also for constructing fusion proteins, facilitating the expression of recombinant proteins, obtaining recombinant proteins that are automatically secreted outside the host cell, or facilitating the purification of recombinant proteins, it is often necessary to add some amino acids to the N-terminus, C-terminus, or other suitable regions within the recombinant protein, for example, including but not limited to, suitable linker peptides, signal peptides, leader peptides, terminal extensions, glutathione S-transferases (GSTs) maltose E-binding protein, Protein A, tags such as 6 His or flag, or the proteolytic enzyme sites of Factor Xa or thrombin or enterokinase.

The present optical sensor may comprise a tryptophan-sensitive polypeptide with a mutation. Such mutations are, for example, mutations at sites such as H13, T71, L84, D93, K105, N117, T130, V170, V192, F202, K214, Y217, K255, T259 and/or I283. Exemplarily, the mutation is selected from one or more of the following: H13F, H13W, T71F, T71W, L84F, L84W, D93F, D93W, K105F, K105W, N117F, N117W, T130F, T130W, V170F, V170W, V192F, V192W, F202W, K214F, K214W, Y217F, Y217W, K255F, K255W, T259F, T259W, I283F and/or I283W. In one or more embodiments, the mutation is selected from one or more of H13F, L84F, L84W, D93F, D93W, K105F, K105W, N117F, N117W, V170F, V170W, V192F, F202W, K214F, K214W, Y217F, Y217W, K255F, K255W, T259F, T259W, I283F and I283W. In one or more embodiments, the mutation is selected from one or more of L84F, K105F, K105W, N117F, V170F, F202W, K214F, K214W, Y217F, Y217W, K255F, K255W, T259F, T259W, I283F and/or I283W.

In an exemplary embodiment, the type B1-A-B2 optical sensor of of the present invention may be a sensor having cpYFP inserted at one or more sites of 31ft selected from the group consisting of: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 or 267/268 and having one or more mutations selected from the group consisting of: H13F, L84F, L84W, D93F, D93W, K105F, K105W, N117F, N117W, V170F, V170W, V192F, F202W, K214F, K214W, Y217F, Y217W, K255F, K255W, T259F, T259W, I283F and I283W. Preferably, the optical sensor is a sensor having cpYFP inserted at one or more sites of 31ft selected from the group consisting of: 263/265, 263/266 or 263/267 and having one or more mutations selected from the group consisting of: L84F, K105F, K105W, N117F, V170F, F202W, K214F, K214W, Y217F, Y217W, K255F, K255W, T259F, T259W, I283F, I283W, and/or I283W. Exemplary sequences are shown in SEQ ID NO: 10-39.

The optical sensors of the present invention comprise any of the amino acid sequence of SEQ ID NO: 6-39 or a variant thereof. In one embodiment, the optical sensors of the present invention comprise sequences having at least 35%, at least 40%, at least 50%, at least 60%, at least 70%, at least 80%, at least 85%, at least 90%, at least 95%, at least 99% sequence identity with any one of the amino acid sequences of SEQ ID NO: 6-39. In a preferred embodiment, the optical sensor provided by the present invention comprises a sequence substantially similar or identical to any of the amino acid sequences SEQ ID NO: 6-39. In a more preferred embodiment, the optical sensor provided by the present invention comprises or consists of any one of SEQ ID NO: 10-39.

The terms "functional fragment", "functional variant", "derivative", and "analog" used herein refer to proteins that maintain essentially the same biological function or activity as the original polypeptide or protein (e.g., a 31ft protein or a fluorescent protein). Functional variants, derivatives, or analogues of a polypeptide or protein (e.g., a 31ft protein or a fluorescent protein) of the invention may be (i) a protein having one or more conservative or nonconservative amino acid residues (preferably conservative amino acid residues) substituted, whereas such substituted amino acid residues may or may not be encoded by the genetic code, or (ii) a protein having a substituted group in one or more amino acid residues, or (iii) a protein formed by the fusion of the mature protein to another compound, such as a compound that extends the half-life of the protein, such as polyethylene glycol, or (iv) a protein formed by the fusion of an additional amino acid sequence to this protein sequence (such as a secretory sequence or the sequence or protein used to purify this protein, or the fusion polypeptide formed with an antigenic IgG fragment). According to the teaching herein, these functional variants, derivatives, and analogues belong to the common knowledge to those skilled in the art.

The difference of said analogues from the original polypeptide or protein may be a difference in amino acid sequence, a difference in modified form that does not affect the sequence, or both. These proteins include natural or induced genetic variants. Induced variants can be derived by various techniques, such as random mutagenesis by radiation or exposure to mutagens and can also be obtained by site directed mutagenesis or other known techniques in molecular biology.

The present fusion polypeptide comprises the optical sensor described herein and an additional polypeptide. In some embodiments, the optical sensor described herein also comprises another polypeptide fused to it. The additional polypeptide described herein does not affect the property of the optical sensor. The additional polypeptide may be located N- and/or C-terminal to the optical sensor. In some embodiments, other polypeptides include polypeptides that localize optical sensors to different organelles or subcellular organelles, tags for purification, or tags for immunoblotting. There may be a linker between the optical sensor and the additional polypeptide in the fusion polypeptide described herein.

The subcellular organelles described here include cytosol, mitochondria, nucleus, endoplasmic reticulum, cell membrane, Golgi apparatus, lysosome, and peroxisome, among others. In some embodiments, the tag for purification or the tag for immunoblotting include 6 histidine (6*His), glutathione sulfurtransferase (GST), Flag.

The expression vector of the present invention comprises the nucleic acid sequence of the present invention or a complementary sequence thereof operably linked to an expression control sequence, the nucleic acid sequence encoding the optical sensor or fusion polypeptide of the present invention. In some embodiments, the expression vector is selected from the group consisting of prokaryotic expression vector, eukaryotic expression vector, and viral vector. In some embodiments, prokaryotic expression vectors are preferably derived from plasmid pCDF operably linked to the nucleic acid sequences described herein. In some embodiments, expression control sequences include origins of replication, promoters, enhancers, operators, terminators, ribosome binding sites.

The present invention also provides a method for preparing the above-mentioned tryptophan optical sensor, comprising the following steps: 1) incorporating the nucleic acid sequence encoding the tryptophan optical sensor described herein into an expression vector; 2) transferring the expression vector into the host cell; 2) culturing the host cell under conditions suitable for the expression of the expression vector, 3) separation of tryptophan optical sensors.

The terms "nucleic acid" or "nucleotide" or "polynucleotide" or "nucleic acid sequence" used herein may be in the form of DNA or in the form of RNA. DNA form includes cDNA, genomic DNA, or artificially synthesized DNA. DNA can be single stranded or double stranded. DNA can be either the coding or noncoding strand. When referring to nucleic acids, the term "variant" used herein may be a naturally occurring allelic variant or a non-naturally occurring variant. These nucleotide variants include degenerate variants, substitution variants, deletion variants, and insertion variants. The nucleic acid of the invention may comprise a nucleotide sequence having sequence identity of at least about 50%, at least about 60%, at least about 70%, at least about 75%, at least about 80%, at least about 85%, at least about 90%, at least about 95%, at least about 98%, at least about 99%, or 100% to the nucleic acid sequence. The invention also relates to a nucleic acid fragment that hybridizes to the sequences described above. In an exemplary embodiment, the nucleic acid sequence is shown in SEQ ID NO: 40, which represents the coding sequence of a sensor with cpYFP inserted into position 263/266 of the functional fragment of tryptophan binding protein and having a T259F mutation. As used herein, a "nucleic acid fragment" is at least 15 nucleotides in length, preferably at least 30 nucleotides, more preferably at least 50 nucleotides, and even more preferably at least 100 nucleotides or more. The nucleic acid fragment can be used in amplification techniques of nucleic acids (such as PCR).

The full-length sequences or fragments thereof of the optical sensors or fusion polypeptide of the invention can often be obtained by PCR amplification, artificial synthesis or recombinant procedures. For PCR amplification, primers can be designed according to the nucleotide sequences disclosed in the invention and the sequences in interest can be amplified with a commercially available cDNA library or a cDNA library prepared by conventional methods known to those skilled in the art as template. When the nucleotide sequence is greater than 2500 bp, it is preferable to perform 2~6 rounds of PCR amplification, and then the individually amplified fragments are spliced together in the correct order. There is no special limit to the procedures and systems for PCR amplification described herein, and conventional PCR amplification procedures and systems in the art may be used. Recombination can also be used to obtain relevant sequences in bulk. This is usually by cloning into a vector, retransferring into cells, and then isolating and purifying the polypeptide or protein in inserest from proliferated host cells by conventional methods. In addition, synthetic methods are also available to synthesize the the sequence in interest, especially for short fragments. In the present invention, when the nucleotide sequence of the optical sensor is less than 2500 bp, it may be synthesized by an artificial synthetic method. The artificial synthetic method is a conventional artificial synthetic method for DNA in the art with no other special requirements. In general, many small fragments are first synthesized, and then ligated to obtain a very long sequence. At present, it has become possible to obtain, entirely by chemical synthesis, DNA sequences encoding the proteins of the invention (or functional variants, derivatives, or analogs thereof). This DNA sequence can then be introduced into a variety of existing DNA molecules known in the art, such as vectors, and into cells. Mutations can be introduced into the protein sequence of the invention by methods such as mutation PCR or chemical synthesis.

The invention also provides a detection test kit comprising an optical sensor or fusion polypeptide or polynucleotide described herein, or an optical sensor or fusion polypeptide prepared according to the method described herein. The kit also optionally contains other reagents required for the detection of tryptophan using an optical sensor. Such other reagents are routinely known in the art.

The invention also relates to a nucleic acid construct containing the polynucleotides described herein, and one or more regulatory sequences operably linked to such sequences. The polynucleotides described herein can be manipulated in a variety of ways to guarantee expression of said polypeptide or protein. The nucleic acid construct can be manipulated according to the difference or requirements of the expression vector prior to insertion of the nucleic acid construct into the vector. Techniques that utilize recombinant DNA methods to alter polynucleotide sequences are known in the art.

In certain embodiments, the nucleic acid construct is a vector. The vector can be a cloning vector, an expression vector, or a gene knock-in vector, such as a homologous recombination vector. The polynucleotides of the present invention can be cloned into many types of vectors, e.g., plasmids, phagemids, phage derivatives, animal viruses, and cosmids. Cloning vectors can be used to provide coding sequences for proteins or polypeptides of the invention. Expression vectors can be provided to cells in the form of bacterial or viral vectors. Expression of the present polynucleotides is generally achieved by operably linking the polynucleotides of the invention to a promoter and incorporating the construct into an expression vector.

This vector may be suitable for replicating and integrating eukaryotic cells. A typical expression vector contains an expression control sequence that can be used to regulate the expression of the desired nucleic acid sequence. Knock-in vectors are used to knock-in or integrate the expression cassettes described herein into the host genome.

The term "expression control sequence" used herein refers to elements that regulate the transcription, translation, and expression of a gene of interest and can be operably linked to the gene of interest, which may be a replication origin, promoter, marker gene, or translational control element, including enhancers, operons, terminators, ribosome binding sites, etc., and the choice of expression control sequence depends on the host cell used. In recombinant expression vectors, "operable ligation" refers to the attachment of the nucleotide sequence of interest to a regulatory sequence in a manner that allows the expression of the nucleotide sequence. Those skilled in the art are well known of methods for constructing expression vectors containing the present fusion polypeptide coding sequences and suitable transcription/translation control signals. These include in vitro recombinant DNA techniques, DNA synthesis techniques, in vivo recombination techniques, etc. Said DNA sequence can be effectively ligated to an appropriate promoter in an expression vector to direct mRNA synthesis. Representative examples of these promoters are: the lac or trp promoter of *E. coli*; λ-phage PL promoter; eukaryotic promoters including the CMV immediate early promoter, the HSV thymidine kinase promoter, the early and late SV40 promoters, the LTR of retroviruses, and several other promoters known to control gene expression in prokaryotic or eukaryotic cells or their viruses. The expression vector also includes a ribosome binding site for translation initiation and a transcription terminator. In one embodiment, the expression vector may use a commercially available pCDF vector with no other special requirements. Exemplarily, HindIII and XhoI were employed to double digest the nucleotide sequence encoding the optical sensor and the expression vector, respectively, and then the enzymatic cleavage products of both were ligated to give recombinant expression vectors. The present invention makes no special limitation to the specific steps and parameters of enzymatic cleavage and ligation, and those conventional in the art would work.

After a recombinant expression vector is obtained, this vector is transformed into host cells to produce a protein or peptide including the fusion protein. This transfer process can be performed with conventional techniques well known to those skilled in the art, such as transformation or transfection. The host cells described herein refer to cells capable of receiving and accommodating recombinant DNA molecules, which are sites of recombinant gene amplification, and ideally the recipient cell should satisfy both conditions of easy access and proliferation. The "host cells" of the invention may include prokaryotic cells and eukaryotic cells, specifically including bacterial cells, yeast cells, insect cells, and mammalian cells. The host cells are said to prefer a variety of cells favouring the expression or fermentative production of the gene product, such cells being well known and commonly used in the art. Those skilled in the art well know how to select appropriate vectors, promoters, enhancers, and host cells.

The methods of transfer to host cells described herein are conventional methods in the art, including calcium phosphate or calcium chloride coprecipitation, DEAE-mannan-mediated transfection, lipofection, naturally competent cells, chemically mediated transfer, or electroporation. When the host is a prokaryote such as *E. coli*, the process described is preferably $CaCl_2$ method or $MgCl_2$ method, and their steps used are well known in the art. When the host cell is a eukaryotic cell, the following DNA transfection methods are used: calcium phosphate coprecipitation, conventional mechanical methods such as microinjection, electroporation, liposome packaging, etc.

After transferring the expression vector into host cells, the host cells transferred with the expression vector are subjected to expansion and expression culture, and the tryptophan optical sensor is isolated. The host cells are expanded for expression by conventional methods. Depending on the host cell species used, the medium used in culture may be various conventional media. Culture is performed under conditions suitable for host cell growth.

In the present invention, an optical sensor is expressed intracellularly, on the cell membrane, or secreted outside the cell. Recombinant proteins can be isolated or purified by various separation methods, if desired, using their physical, chemical, and other properties. The present invention does not have a special limit to a process for separating said tryptophan fluorescent proteins, and a conventional method for the isolation of fusion proteins in the art would work. These methods are well known to those skilled in the art and include, but are not limited to: conventional renaturation treatments, salting out methods, centrifugation, osmotic disruption, sonication, ultra centrifugation, molecular sieving chromatography, adsorption chromatography, ion exchange chromatography, high performance liquid chromatography (HPLC) and other liquid chromatography techniques and the combination of these methods. In one embodiment, His tag affinity chromatography is utilized for optical sensor isolation.

The invention also provides use of said tryptophan optical sensors in real-time localization, quantitative detection of tryptophan as well as high-throughput compound screening. In one aspect, said tryptophan optical sensor, preferably linked with signal peptides at different parts of the cell, is transferred into cells for real-time localization of tryptophan by detecting the strength of fluorescence signals in cells; corresponding quantitative detection of tryptophan is performed by a tryptophan standard titration curve. The tryptophan standard titration curve described herein is plotted from the fluorescence signals of a tryptophan optical sensor in the presence of different concentrations of tryptophan. The tryptophan optical sensor described herein is directly transferred into cells, which is more accurate without time-consuming sample processing process during the real-time localization and quantitative detection of tryptophan. The present tryptophan optical sensor, when performing high-throughput compound screening, adds different compounds to the cell culture fluid, determines changes in tryptophan content, and thus screens out compounds that influence the changes in tryptophan content. The use of the tryptophan optical sensors described herein in real-time localization, quantitative detection of tryptophan as well as high-throughput compound screening are all non-diagnostic and therapeutic purposes, not related to the diagnosis and treatment of diseases.

Concentrations, contents, percentages, and other values may be expressed with ranges available herein. It is also understood that use of these ranges is only for convenience and conciseness, which should be interpreted elastically to include values explicitly mentioned in the upper and lower limits of the range, but also to include all individual values or sub ranges included in the ranges.

EXAMPLE

The tryptophan optical sensors provided by the invention are described in detail below in combination with the examples, but they cannot be understood as defining the scope of protection of the invention.

I. Experimental Materials and Reagents

The conventional molecular biology cloning methods for genetic engineering and cell culture and imaging methods mainly used in examples are well known to those skilled in the art, for example, Roskams, J., *Molecular Biology Laboratory Handbook*; J. Sambrook, D. W. Russell ed, *Molecular Cloning: A Laboratory Manual*, translated by Peitang Huang et al. (3rd edition, August 2002, Science Press); R. I. Freshney et al., *Culture of Animal Cells: a Manual of Basic Technique* (5th edition), translated by Jingbo Zhang and Cunquan Xu; Juan S. Bonifacino, M. Daso, et al., *Short Protocols in Cell Biology*, translated by Jingbo Zhang et al.

The pCDF-cpYFP based, pCDF-tryptophan binding protein plasmid used in examples was constructed by the Protein Laboratory of East China University of Science and Technology, and the pCDF plasmid vector was purchased from Invitrogen. All the primers used for PCR were synthesized, purified, and identified to be correct by mass spectrometry (MS) by Shanghai Generay Biotech Co., Ltd. The expression plasmids constructed in examples were all sequenced by BGI and Jie Li Sequencing. For each example, Taq DNA polymerase was purchased from Dongsheng Bio, pfu DNA polymerase was purchased from Tiangen Biochemical Technology (Beijing) Co., Ltd, primeSTAR DNA polymerase was purchased from Takara, and all three polymerases were purchased with corresponding polymerase buffer and dNTPs. Restriction enzymes such as BamHI, BglII, HindIII, NdeI, XhoI, EcoRI, SpeI, T4 ligase, and T4 phosphorylase (T4 PNK) were purchased from Fermentas with corresponding buffers and the like. Transfection reagent Lip2000 Kit was purchased from Invitrogen. Amino acids such as tryptophan were purchased from Sigma. Chemical reagents such as inorganic salts were purchased from Sigma-Aldrich unless specifically stated. HEPES salt, Ampicillin (Amp), and puromycin were purchased from Ameresco. 96 well detection black plates, 384 well fluorescence detection black plates were purchased from Grenier.

The DNA purification kit used in examples was purchased from BBI (Canada), and the common Plasmid Mini Preparation Kit was purchased from Tiangen Biochemical Technology (Beijing) Co., Ltd. Clonal strain Mach1 was purchased from Invitrogen. Nickel column affinity chromatography columns and desalting column packing were from GE Healthcare.

The main instruments used in examples include: Biotek Synergy 2 multi-purpose microplate reader (Bio-Tek, USA), X-15R high-speed refrigerated centrifuge (Beckman, USA), Microfuge22R tabletop high-speed refrigerated centrifuge (Beckman, USA), PCR amplimer (Biometra, Germany), ultrasonic disruptor (Ningbo SCIENTZ), nucleic acid electrophoresis instrument (Shennengbocai company), spectrofluorometer (Varian, USA), $CO_2$ constant temperature cell culture incubator (SANYO), and inverted fluorescence microscope (Nikon, Japan).

II. Molecular Biology Methods and Cellular Experimental Methods

II.1 Polymerase Chain Reaction (PCR):

1. PCR Amplification of Target Fragments:

This method was mainly used for gene fragment amplification and colony PCR to identify positive clones. The reaction system for PCR amplification was as follows: template sequence 0.5-1 μL, the forward primer (25 μM) 0.5 μL, the reverse primer (25 μM) 0.5 μL, 10×pfu buffer 5 μL, pfu DNA polymerase 0.5 μL, dNTP (10 mM) 1 μL, sterilized ultrapure water (ddH2O) 41.5-42 μL, to a total volume of 50 μL. The PCR amplification program was as follows: denaturation at 95° C. for 2-10 min, 30 cycles (94-96° C. for 30-45 s, 50-65° C. for 30-45 s, 72° C. for a period (600 bp/min)), and extension at 72° C. for 10 min.

2. PCR Amplification of Long Fragments (>2500bp):

Long fragment amplification, primarily inverse PCR amplification vector, used in the invention is a technique used to obtain site directed mutations in examples below. Reverse PCR primers were designed at the variation site, where the 5' end of one primer contained the variant nucleotide sequence. Amplified products contained the corresponding mutation site. The reaction system of amplification PCR of long fragments were as follows: template sequence (10 pg-1 ng) 1 μL, the forward primer (25 μM) 0.5 μL, the reverse primer (25 μM) 0.5 μL, 5× PrimerSTAR buffer 10 μL, PrimerSTAR DNA polymerase 0.5 μL, dNTPs (2.5 mM) 4 μL, sterilized ultrapure water (ddH2O) 33.5 μL, to a total volume of 50 μL. The PCR amplification program was as follows: denaturation at 95° C. for 5 min, 30 cycles (98° C. for 10 s, 50-68° C. for 5-15 s, 72° C. for a period (1000 bp/min)), and extension at 72° C. for 10 min; or denaturation at 95° C. for 5 min, 30 cycles (98° C. for 10 s, 68° C. for a period (1000 bp/min)), and extension at 72° C. for 10 min.

II.2 Endonuclease Digestion Reaction:

The system for double digestion of plasmid vectors was as follows: plasmid vector 20 μL (approximately 1.5 μg), 10× Buffer 5 μL, restriction endonuclease 11-2 μL, restriction endonuclease 21-2 μL, made up to a total volume of 50 μlL with sterilized ultrapure water. Reaction condition is 37° C. for 1-7 hours.

II.3 5' Phosphorylation Reaction of DNA Fragments

The ends of plasmids or genomes extracted from microorganisms contain phosphate groups, but PCR products do not contain. Therefore, it is necessary to perform phosphate group addition reaction on the 5'-end bases of PCR products, only DNA molecules containing phosphate groups at the ends can occur ligation reaction. The phosphorylation reaction system is as follows: PCR product fragment DNA sequence 5-8 μL, 10×T4 polynucleotide buffer 1 μL, T4 polynucleotide (T4 μL 1 μL), phosphorylation reaction ligation ultrapure water 0-3 μL, total volume 10 μL. The reaction conditions were 37° C., inactivation at 72° C. for 20 minutes after 30 minutes to 2 hours.

II.4 Ligation of Target Fragments and Vectors

There are differences in the ligation method between different fragments and vectors, and three ligation methods are used in this invention.

1. Ligation of Blunt End Short Fragments and Linearized Vectors

The principle of this method is that the blunt end product obtained by PCR, after phosphorylation of the 5' end of the DNA fragment by T4 PNK, is ligated with a linearized vector in the presence of PEG4000 and T4 DNA ligase to obtain a recombinant plasmid. The homologous recombination ligation system was as follows: T4 PNK treated DNA fragment 4 μL, linearized vector fragment 4 μL, PEG4000 μL, 10×T4 ligase buffer 1 μL, T4 DNA ligase 1 μL, to total of 10 μL. The reaction condition was 22° C. for 30 min.

2. Ligation of DNA Fragments Containing Cohesive Ends and Vector Fragments Containing Cohesive Ends DNA fragments cut by restriction endonucleases usually produce sticky ends that stick out, so they can be ligated with vector fragments containing complementary sticky ends to form recombinant plasmids. The ligation reaction system is as follows: 1-7 μL of PCR product fragment DNA after digestion, 0.5-7 μL of plasmid after digestion, 1 μL of 10×T4 ligase buffer, 1 μL of T4 DNA ligase, and sterilized ultrapure water to make up the total volume 10 μL. Reaction condition was 16° C., 4-8 hours.

3. Ligation Reactions in which the Products of DNA Fragments Phosphorylated at the 5' End were Self Circularized After Site Directed Mutagenesis Were Introduced by Inverse PCR The 5'-end phosphorylated DNA fragment is ligated to the 3'-end and 5'-end of the linearized vector through self-circularization ligation reaction to obtain a recombinant plasmid. The self-cyclization ligation reaction system is as follows: phosphorylation reaction system 10 μL, T4 ligase (5 U/μL) 0.5 μL, total volume 10.5 μL. Reaction condition was 16° C., 4-16 hours.

II.5 Preparation and Transformation of Competent Cells

Preparation of Competent Cells:

1. A single colony (e.g., Mach1) is picked and inoculated in 5 ml LB medium at 37° C. on a shaker overnight.

2. 0.5-1 ml of overnight cultured broth was taken and transferred into 50 ml LB medium and incubated at 37° C. at 220 rpm for 3 to 5 hours until the OD600 reached 0.5.

3. The cells were precooled in ice bath for 2 hours.

4. 4° C., centrifugation at 4000 rpm for 10 min.

5. The supernatant was discarded, the cells were resuspended with 5 ml of precooled buffer, and resuspension buffer was added again after homogenization to a final volume of 50 ml.

6. Ice bath for 45 min.

7. 4° C., centrifugation at 4000 rpm for 10 min, the bacteria were resuspended with 5 ml ice precooled storage buffer.

8. 100 μL of broth was loaded to each EP tube and frozen at −80° C. or in liquid nitrogen.

Resuspension buffer: $CaCl_2$ (100 mM), $MgCl_2$ (70 mM), NaAc (40 mM) Storage buffer: 0.5 mL DMSO, 1.9 mL 80% glycol, 1 mL 10×$CaCl_2$ (1 M), 1 mL 10×$MgCl_2$ (700 mM), 1 mL 10×NaAc (400 mM), 4.6 mL dd$H_2O$ Transformation of Compenent Cells:

1. Take 100 μL competent cells were taken and thawed on an ice bath.

2. The appropriate volume of ligation product was added, mixed by gently pipetting, and incubated in ice bath for 30 min. The volume of ligation product normally added was less than 1/10 of the volume of competent cells.

3. The broth was put into a 42° C. water bath for heat shock for 90 s and quickly transferred to an ice bath for 5 min.

4. 500 μL LB was added and incubated at 200 rpm on a constant temperature shaker at 37° C. for 1 hour.

5. The broth was centrifuged at 4000 rpm for 3 min and 200 μL supernatant was added to mix the bacteria well and spread evenly on the surface of the agar plate containing appropriate antibiotics, and the plate is inverted in a 37° C. incubator overnight.

II.6 Expression, Purification, and Fluorescent Detection of Proteins

1. The expression vectors (such as a pCDF-based tryptophan optical sensor expression vector) were transformed into BL21 (DE3) cells, incubated inverted overnight, and the clones were picked from the plates into 250 ml Erlenmeyer flasks, placed in a shaker at 37° C. and incubated at 220 rpm to OD=0.4-0.8, then 1/1000 (V/V) of IPTG (1 M) was added to induce expression at 18° C. for 24-36 hours.

2. Upon completion of inducible expression, cells were harvested by centrifugation at 4000 rpm for 30 min, resuspended in 50 mM phosphate buffer and disrupted ultrasonically until the broth were clear, centrifuged at 9600 rpm at 4° C. for 20 min. Centrifuge at 9600 rpm, 4° C. for 20 minutes.

3. The centrifuged supernatant was purified by a self-packed nickel-column affinity chromatography column to obtain the protein, and the protein after nickel-column affinity chromatography was then passed through a self-packed desalting column to obtain the protein dissolved in 100 mM HEPES buffer (pH 7.4).

4. After the purified protein was identified by SDS-PAGE, the sensor was diluted with assay buffer (100 mM HEPES, 100 mM NaCl, pH 7.4) into a protein solution with a final concentration of 0.2-5 μM. Tryptophan was prepared as a stock solution at a final concentration of 50 mM with assay buffer (100 mM HEPES, 100 mM NaCl, pH 7.4).

5. Take 100 μL of 1 μM protein solution, incubate at 37° C. for 10 minutes, add tryptophan for titration, and measure the fluorescence intensity of the protein at 528 nm after excitation at 420 nm and at 528 nm after excitation at 485 nm. The fluorescence excitation and emission measurement of the samples were completed by a multifunctional fluorescence microplate reader.

6. Take 100 μL of 1 μM protein solution, incubate at 37° C. for 10 minutes, add tryptophan, and measure the absorption and fluorescence spectra of the protein. The determination of the absorption spectrum and fluorescence spectrum of the sample is completed by a spectrophotometer and a fluorescence spectrophotometer.

II.6 Expression, Purification, and Fluorescent Detection of Proteins

1. The pCDNA3.1+-based tryptophan optical sensor plasmid was transfected into HeLa by the transfection reagent Lipofectamine2000 (Invitrogen), and cultured in a cell incubator at 37° C., 5% $CO_2$. Fluorescence detection was performed 24-36 h after the exogenous gene was fully expressed.

2. After induction of expression, adherent HeLa cells were washed three times with PBS and placed in HMS solution for fluorescence microscopy and microplate reader assays, respectively.

Example 1

Tryptophan Binding Protein Plasmid

The 31ft gene in the *Streptococcus pneumoniae* gene was amplified by PCR, and the PCR product was recovered after gel electrophoresis and digested with HindIII and XhoI, and the pCDF vector was subjected to corresponding double digestion. After ligation with T4 DNA ligase, DH5a was transformed with the product, and the transformed DH5a was spread on LB plate (streptomycin 100 ug/mL) and incubated at 37° C. overnight. After growing DH5a transformants were subjected to plasmid extraction, they were subjected to PCR. Positive plasmids were sequenced to be correct for subsequent plasmid construction.

Example 2

Expression and Detection of Optical Sensors with cpYFP Inserted at Different Sites In this example, based on pCDF-31ft, the insertion of cpYFP at the following sites was selected according to the crystal structure of tryptophan-binding protein to obtain the corresponding pCDF-31ft-cpYFP plasmid: 114/115, 114/116, 114/117, 114/118, 115/116, 115/117, 115/118, 116/117, 116/118, 117/118, 233/234, 233/235, 234/235, 263/264, 263/265, 263/266, 263/267, 263/268, 264/265, 264/266, 264/267, 264/268, 265/266, 265/267, 265/268, 266/267, 266/268 and/or 267/268. Exemplary sequences are shown in Table 1.

TABLE 1

Sequences of optical sensors

| Sequences | Insertion site |
|---|---|
| SEQ ID NO: 6 | 263/265 |
| SEQ ID NO: 7 | 263/266 |
| SEQ ID NO: 8 | 263/267 |
| SEQ ID NO: 9 | 263/268 |

The DNA fragment of cpYFP was generated by PCR, and the cpYFP terminal homologous sequence was introduced at 5' end through primers. The pCDF-tryptophan-binding protein linearized vector was generated by PCR, which carry completely identical sequences (15 bp to 20 bp) at 5' and 3' ends corresponding to the two ends of cpYFP, respectively. The linearized pCDF-31ft and cpYFP fragments were subjected to homologous recombination under the action of Hieff Clone Enzyme. The product was transformed into DH5a, and the transformed DH5a was spread on LB plate (streptomycin 100 ug/mL) and cultured at 37° C. overnight. The positive clones identified by PCR were sequenced after extraction of plasmids. Sequencing was performed by Jie Li Biology Company.

After being sequenced correctly, the recombinant plasmid was transformed into JM109(DE3) to induce expression, and the protein was purified, and the size was around 63 Kda by SDS-PAGE. This size corresponds to the size of the 31ft-cpYFP fusion protein containing His-tag purified label expressed from pCDF-31ft-cpYFP. The results are shown in FIG. 1.

Figure 2:
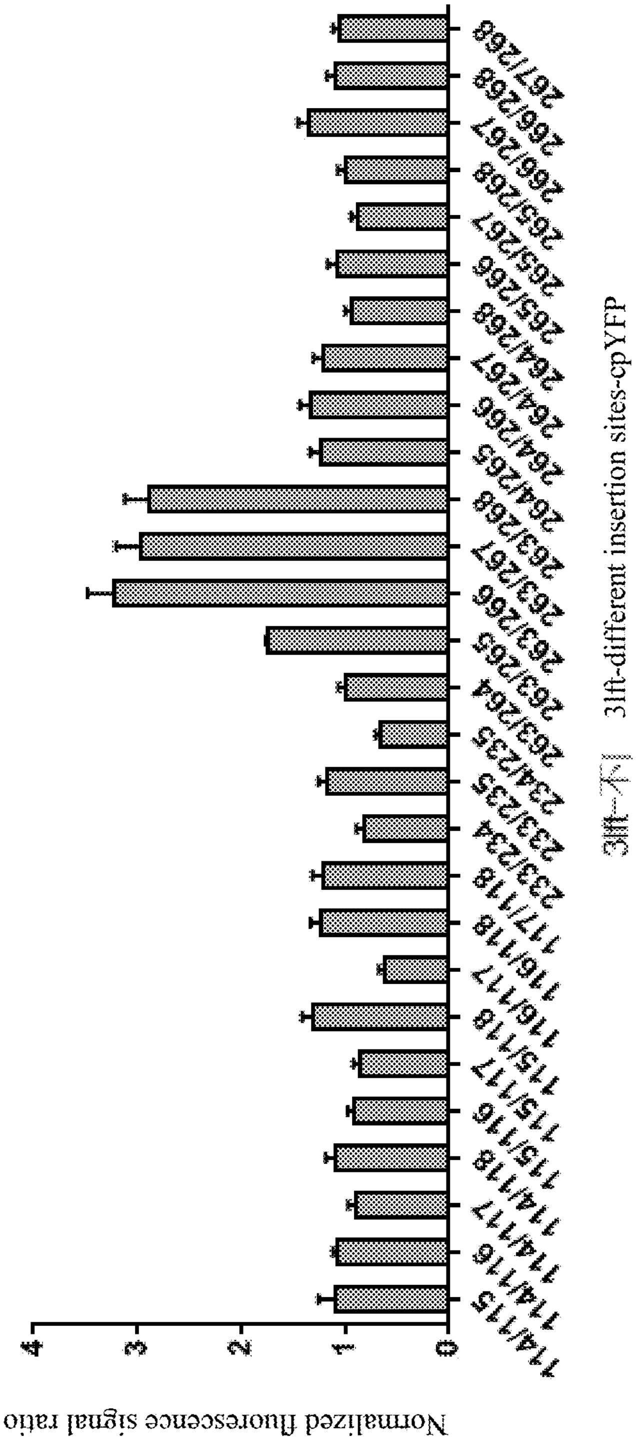
FIG. 2 is a graph of the response change of the exemplary tryptophan optical sensor to tryptophan described in Example 2, the sensor comprises cpYFP and tryptophan-binding protein.

Tryptophan response screening was performed with disrupted supernatants of *E. coli* expressing the 31ft-cpYFP fusion protein, and the detection signal of the fusion fluorescent protein containing 1 mM tryptophan was divided by the detection signal of the fusion fluorescent protein without tryptophan. The results are shown in FIG. 2. The detection results show that the optical sensors that respond more than 1.5 times to tryptophan than control have insertion sites of 263/265, 263/266, 263/267 and 263/268 or the corresponding amino acid positions of their family proteins.

Example 3

Figure 3:
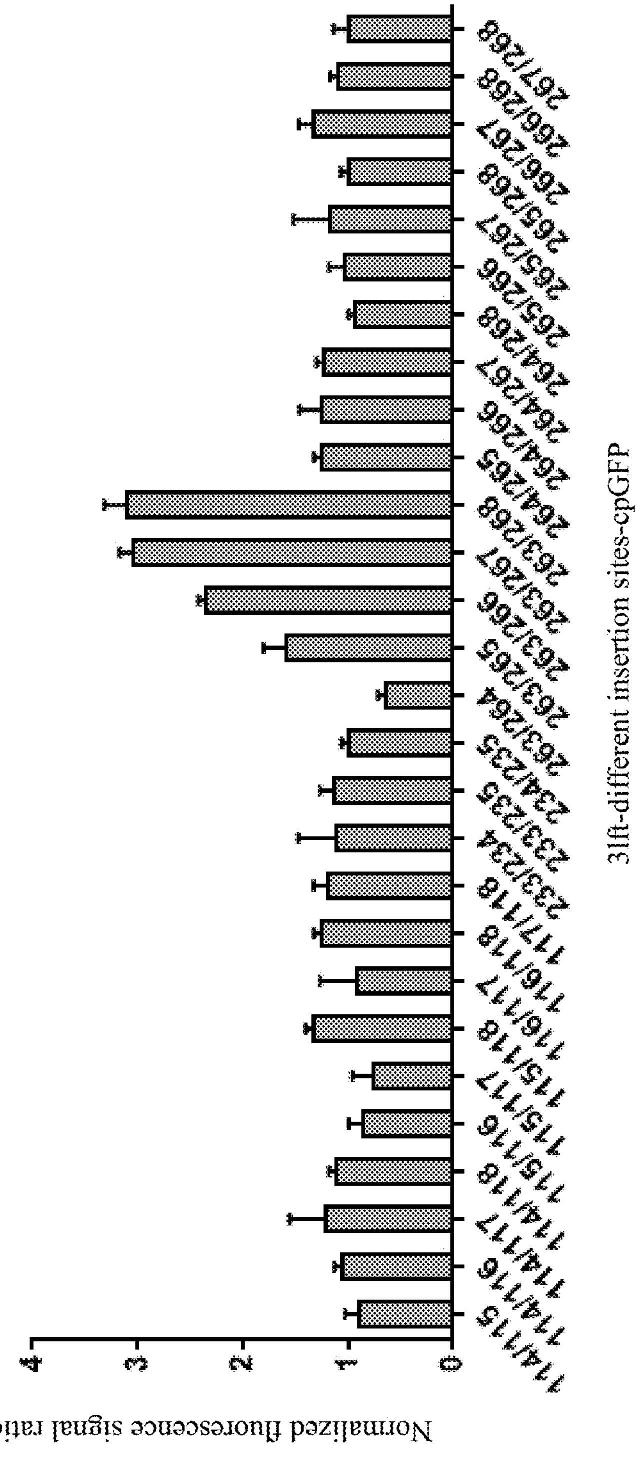
FIG. 3 is a graph of the response change of the exemplary tryptophan optical sensor comprising cpGFP and tryptophan-binding protein to tryptophan described in Example 3.

Expression and Detection of cpGFP Optical Sensors with Different Insertion Sites According to the method in Example 2, cpYFP was replaced with cpGFP to construct a tryptophan green fluorescent protein fluorescent sensor. The results are shown in FIG. 3, test with disrupted supernatant shows that the optical sensors that respond more than 1.5 times to tryptophan have insertion sites of 263/265, 263/266, 263/267 and 263/268 or the corresponding amino acid positions of their family proteins.

Example 4

Figure 4:
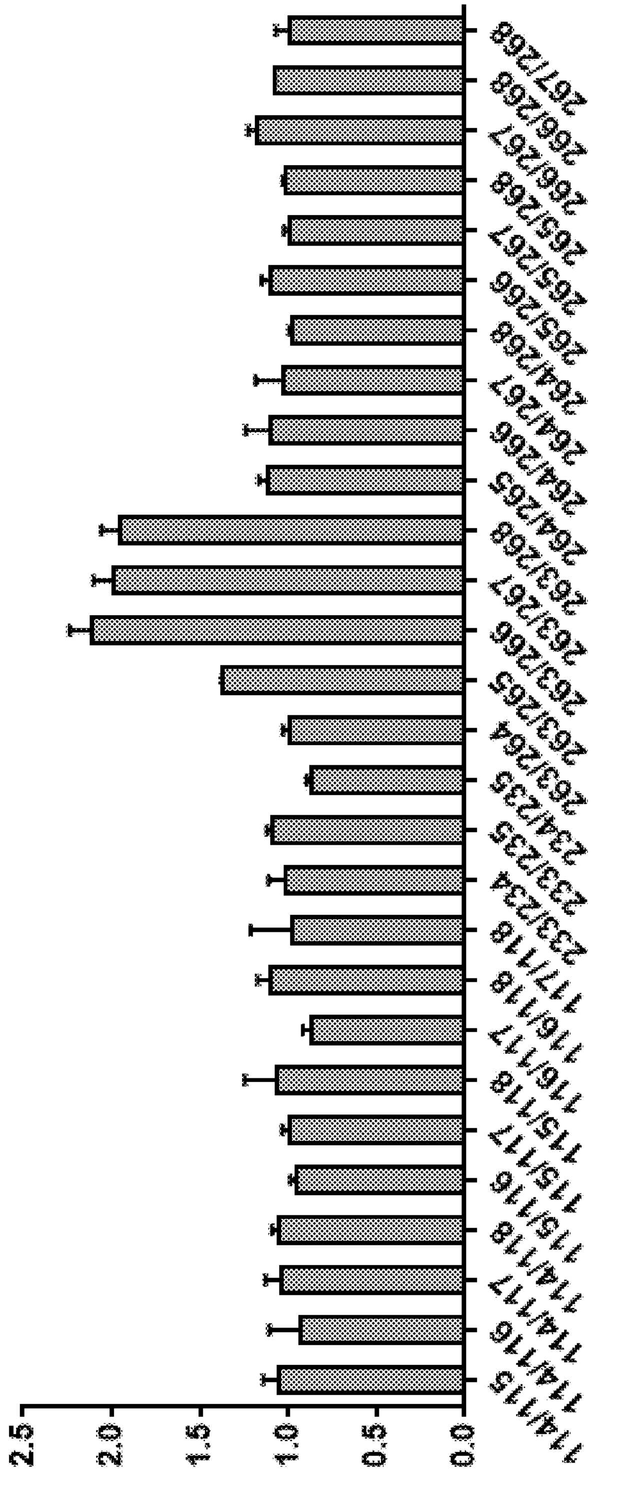
FIG. 4 is a graph of the response change of the exemplary tryptophan optical sensor comprising cpBFP and tryptophan-binding protein to tryptophan described in Example 4.

Expression and Detection of Optical Sensors Having cpBFP Inserted at Different Sites According to the method in Example 2, cpYFP was replaced with cpBFP to construct a tryptophan blue fluorescent protein fluorescent sensor. The results are shown in FIG. 4, test with disrupted supernatant shows that the optical sensors that respond more than 1.5 times to tryptophan have insertion sites of 263/266, 263/267, and 263/268 or the corresponding amino acid positions of their family proteins.

Example 5

Figure 5:
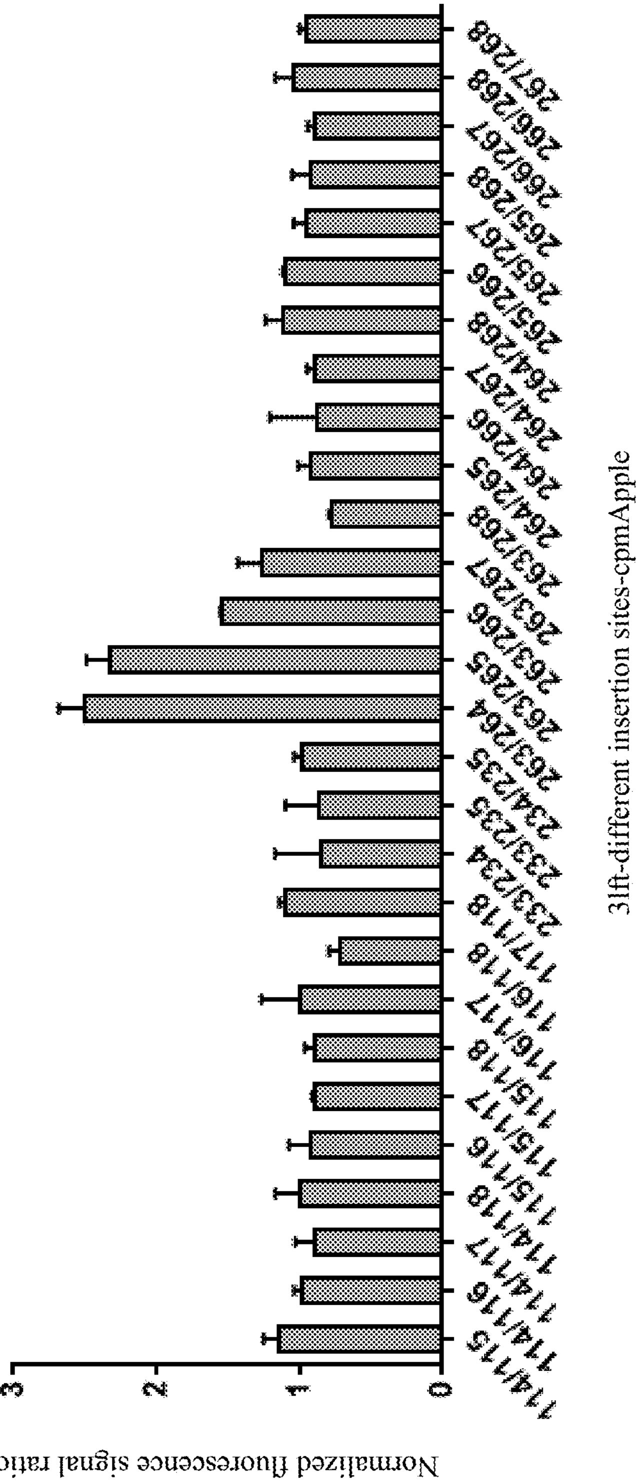
FIG. 5 is a graph of the response change of the exemplary tryptophan optical sensor comprising cpmApple and tryptophan-binding protein to tryptophan described in Example 5.

Expression and Detection of Optical Sensors Having cpmApple Inserted at Different Sites According to the method in Example 2, cpYFP was replaced with cpmApple to construct a tryptophan red fluorescent protein fluorescent sensor. The results are shown in FIG. 5, test with disrupted supernatant shows that the optical sensors that respond more than 1.5 times to tryptophan have insertion sites of 263/264, 263/265, and 263/266 or the corresponding amino acid positions of their family proteins.

Example 6

Performance of Optical Sensors

Figure 6:
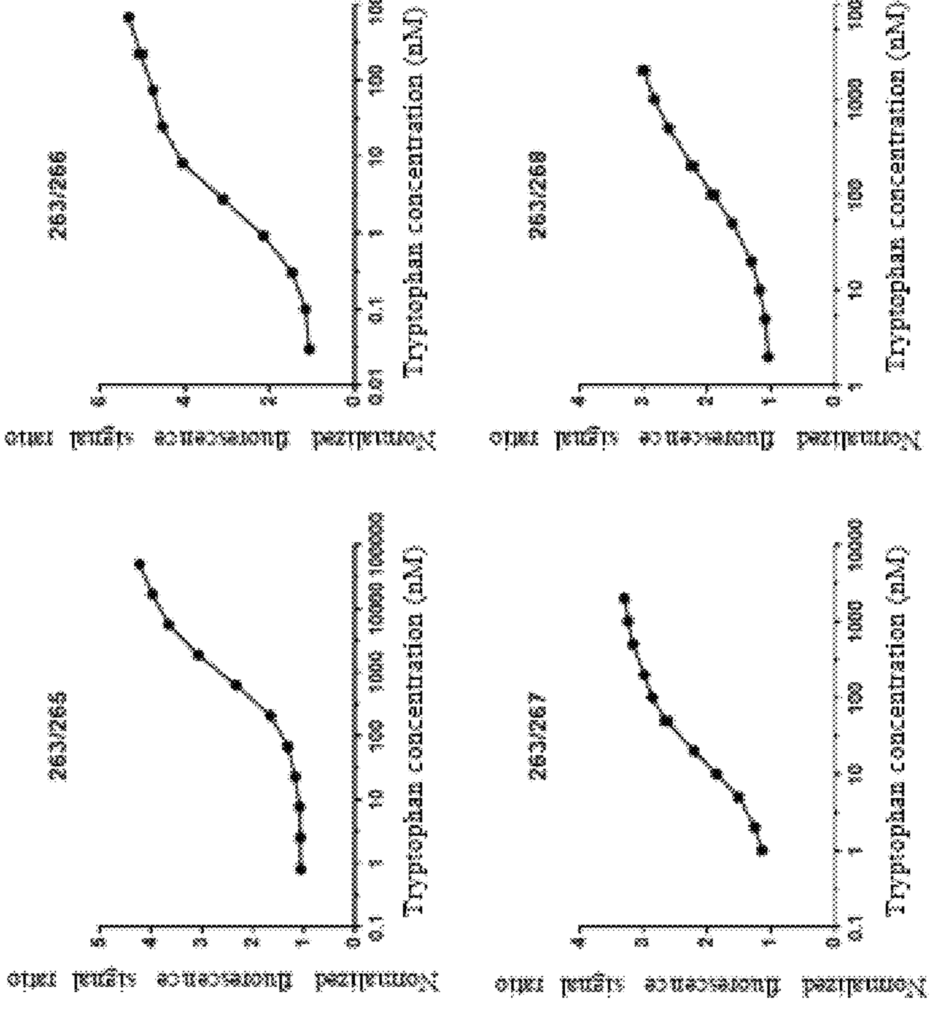
FIG. 6 is the titration curve of the exemplary tryptophan optical sensor to different concentrations of tryptophan described in Example 6.
Figure 7:
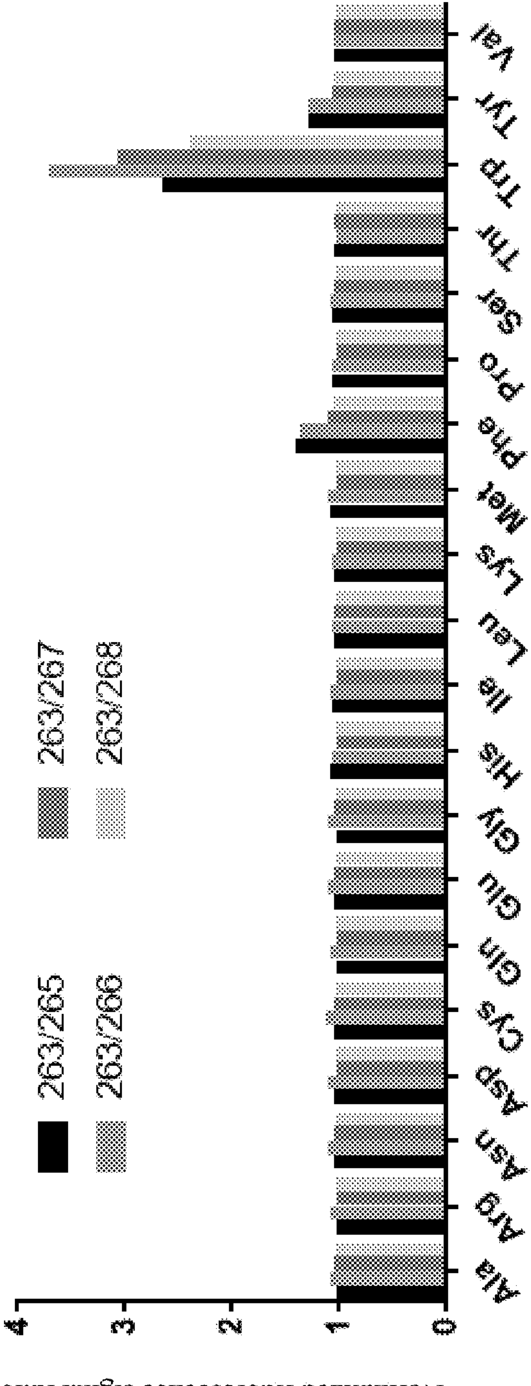
FIG. 7 is a bar graph of the specific detection of 20 amino acids by the exemplary tryptophan optical sensor described in Example 6.

For the optical sensors obtained in Example 2 that responded more than 1.5 times to tryptophan, that is, four optical sensors with insertion site of 263/265, 263/266, 263/267 and 263/268, protein purification and concentration gradient tryptophan detection were performed to detect the change in the ratio of the fluorescence intensity at 528 nm emission excited at 420 nm to that at 528 nm emission excited 485 nm. The Kd (binding constant) of the four tryptophan optical sensors with insertion sites of 263/265, 263/266, 263/267 and 263/268 were 1.6 μM, 7.2 μM, 48 μM and 152 μM, respectively. The change amplitudes are 4.2 times, 5.3 times, 3.3 times and 3.0 times, respectively, and the results are shown in FIG. 6. For sensors with insertion sites of 263/265, 263/266, 263/267 and 263/268 (i.e. 31ft-263/265-cpYFP, 31ft-263/266-cpYFP, 31ft-263/267-cpYFP and 31ft-263/268-cpYFP), specific detection for each amino acid were performed. The results showed that the sensors with insertion sites of 263/265 and 263/266 had similar responses to phenylalanine and tyrosine, 1.37 times and 1.25 times for 263/265, 1.34 times and 1.26 times for 263/266, respectively; and there was no response to amino acids other than tryptophan, phenylalanine and tyrosine. Sensors with insertion sites of 263/267 and 263/268 did not respond to other amino acids than tryptophan, as shown in FIG. 7.

Example 7

Expression and Detection of Mutated cpYFP Optical Sensors

Optical sensor mutants were constructed on the basis of 31ft-263/265-cpYFP, 31ft-263/266-cpYFP, 31ft-263/267-cpYFP. The plasmids pCDF-31ft-263/265-cpYFP, pCDF-31ft-263/266-cpYFP, pCDF-31ft-263/267-cpYFP were linearized by PCR with the primers containing the base sequence of the desired mutation site.

Phosphorus was added to the obtained PCR products under the action of PNK, T4 DNA ligase and PEG4000, thereby obtaining mutant plasmids of 15 sites of H13, T71, L84, D93, K105, N117, T130, V170, V192, F202, K214, Y217, K255, T259, 1283, and the sequencing was completed by Jie Li Sequencing Company. The sequences of some mutated optical sensors are shown in Table 2. An exemplary nucleic acid sequence is set forth in SEQ ID NO:40 (263/266-T259F).

TABLE 2

Sequences of mutated optical sensors

| Sequences | Insertion site | Mutation site |
|---|---|---|
| SEQ ID NO: 10 | 263/265 | L84F |
| SEQ ID NO: 11 | 263/265 | K105F |
| SEQ ID NO: 12 | 263/265 | F202W |
| SEQ ID NO: 13 | 263/265 | K214F |
| SEQ ID NO: 14 | 263/265 | K214W |
| SEQ ID NO: 15 | 263/265 | Y217F |
| SEQ ID NO: 16 | 263/265 | Y217W |
| SEQ ID NO: 17 | 263/265 | K255F |
| SEQ ID NO: 18 | 263/265 | K255W |
| SEQ ID NO: 19 | 263/265 | T259F |
| SEQ ID NO: 20 | 263/265 | T259W |
| SEQ ID NO: 21 | 263/265 | I283F |
| SEQ ID NO: 22 | 263/265 | I283W |

TABLE 2-continued

Sequences of mutated optical sensors

| Sequences | Insertion site | Mutation site |
|---|---|---|
| SEQ ID NO: 23 | 263/266 | L84F |
| SEQ ID NO: 24 | 263/266 | K105F |
| SEQ ID NO: 25 | 263/266 | K105W |
| SEQ ID NO: 26 | 263/266 | F202W |
| SEQ ID NO: 27 | 263/266 | K214F |
| SEQ ID NO: 28 | 263/266 | K214W |
| SEQ ID NO: 29 | 263/266 | Y217F |
| SEQ ID NO: 30 | 263/266 | K255W |
| SEQ ID NO: 31 | 263/266 | T259F |
| SEQ ID NO: 32 | 263/266 | T259W |
| SEQ ID NO: 33 | 263/266 | I283F |
| SEQ ID NO: 34 | 263/267 | L84F |
| SEQ ID NO: 35 | 263/267 | K105F |
| SEQ ID NO: 36 | 263/267 | K105W |
| SEQ ID NO: 37 | 263/267 | F202W |
| SEQ ID NO: 38 | 263/267 | Y217F |
| SEQ ID NO: 39 | 263/267 | T259F |

Figure 8:
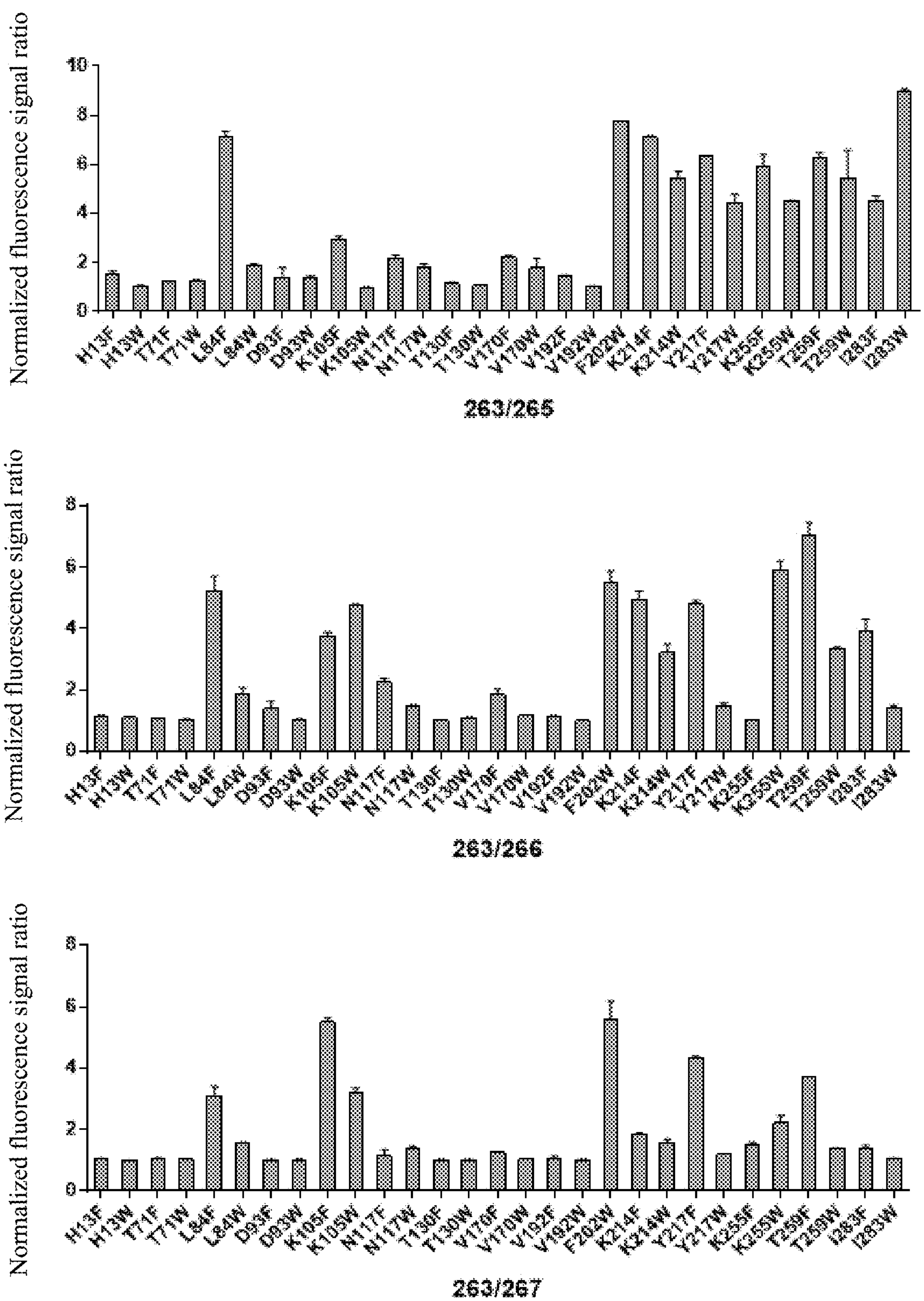
FIG. 8 is a bar graph of the response to tryptophan of the exemplary mutated tryptophan optical sensor described in Example 7.

The results are shown in FIG. 8. Fluorescence detection of purified proteins showed that L84F, F202W, K214F, K214W, Y217F, Y217W, K255F, K255W, T259F, T259W, I283F and I283W mutants responded more than 2.5 times to tryptophan.

Example 8

Spectral Properties, Titration Curves and Specificity of Optical Sensor Mutants Detection of fluorescence spectra was performed using a fluorescence spectrophotometer after subjecting purified tryptophan optical sensor 31ft-263/266-cpYFP-T259F to 0 mM and 1 mM tryptophan treatments for 10 min, respectively.

Figure 9:
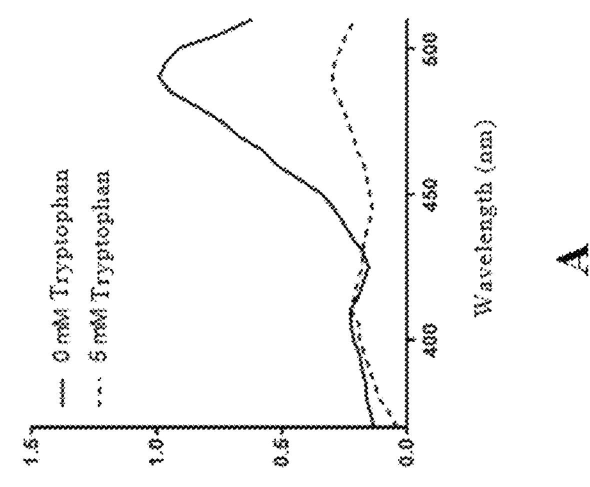
FIGS. 9A-9C are graphs of the fluorescence spectral properties of the exemplary tryptophan optical sensor described in Example 8.
Figure 9:
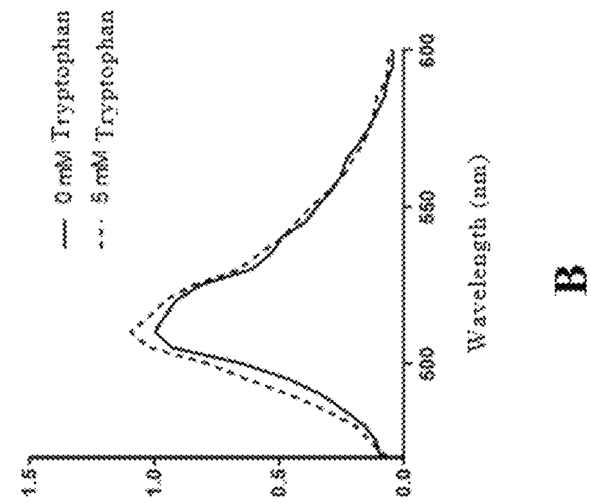
Figure 9:
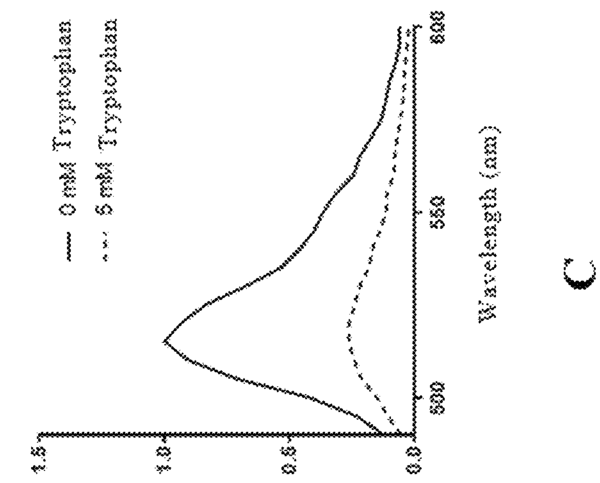

Determination of excitation spectra: Excitation spectra were recorded with an excitation range of 370 nm to 510 nm and an emission wavelength of 530 nm, with readings every 5 nm. The results show that the sensor has two excitation peaks at about 410 and 490 nm, as shown in FIG. 9A.

Determination of emission spectra: excitation spectra were recorded with an fixed excitation wavelength of 420 nm and 485 nm and an emission range of 470-600 nm and 490-600 nm, read every 5 nm. The results showed that after adding 1 mM tryptophan, the fluorescence intensity of the sensor excited at 420 nm was slightly increased to 1.1 times that of adding 0 mM tryptophan; and the decrease in fluorescence intensity under excitation at 460 nm was 0.26-fold compared to that of adding 0 mM tryptophan. As shown in FIGS. 9B and 9C.

Figure 10A:
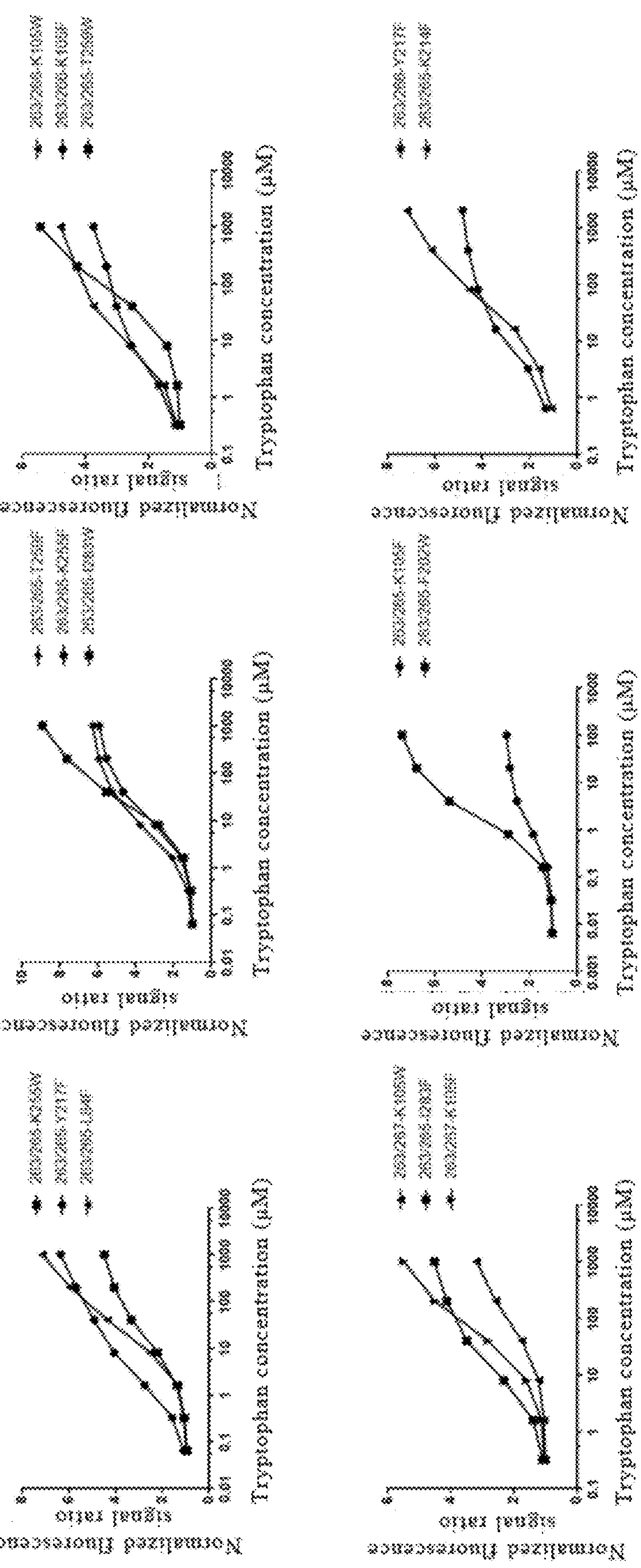
FIG. 10A and FIG. 10B are the titration curve of the exemplary tryptophan optical sensor described in Example 8 to different concentrations of tryptophan.
Figure 10B:
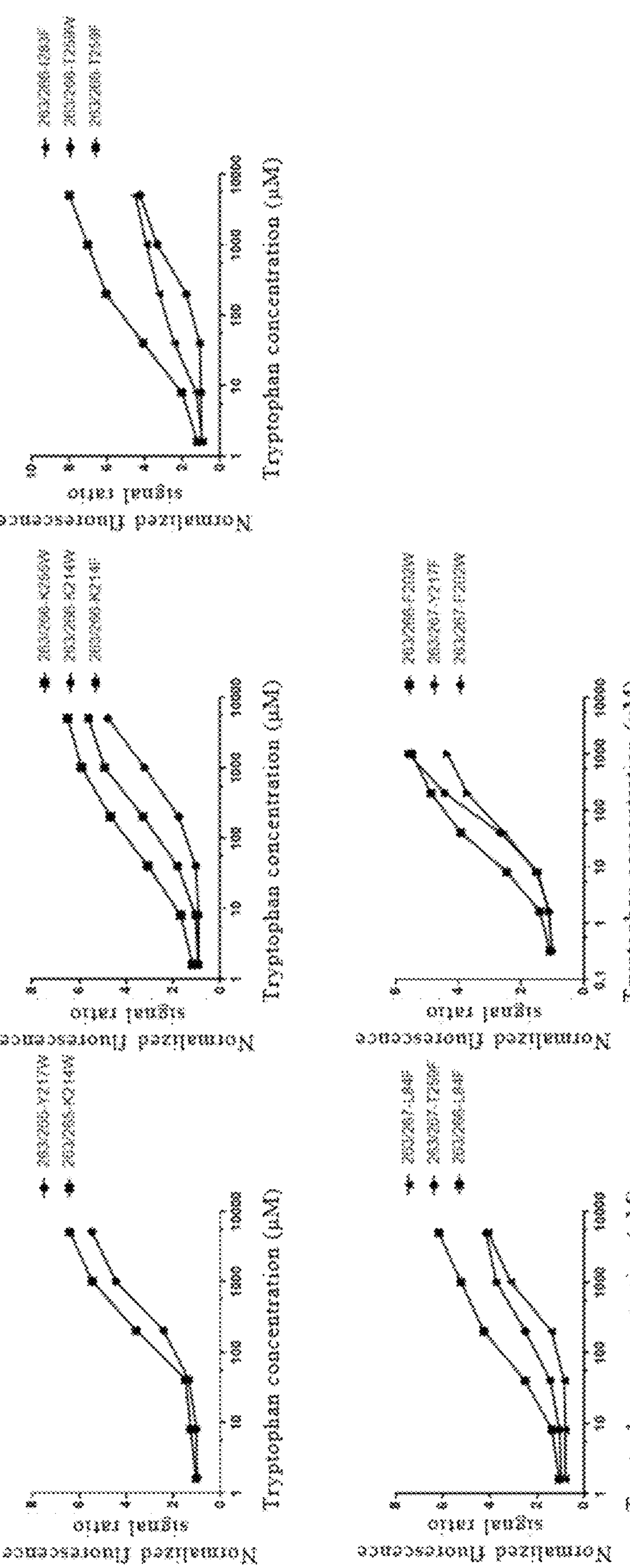

Thirty proteins, such as purified 31ft-263/266-cpYFP-T259F, which responded more than 2.5-fold to tryptophan, were detected by concentration gradient (0-5 mM) tryptophan. After the purified sensor was treated for 10 minutes, the change in the ratio of the fluorescence intensity at 528 nm emission excited at 420 nm and that at 528 nm emission excited at 485 nm was detected. The results are shown in FIG. 10. The Kd (binding constant) of the 30 tryptophan optical sensors varied from 1.1 μM to 133 μM.

Figure 11:
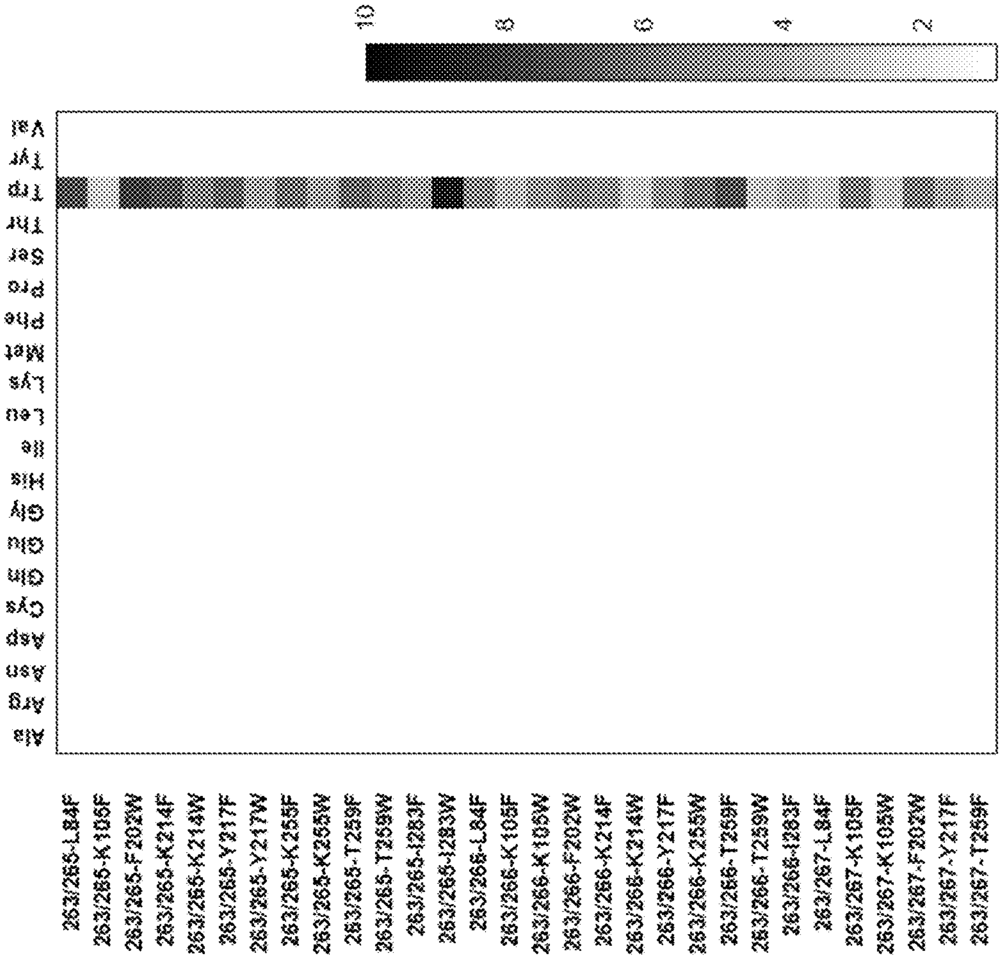
FIG. 11 is a bar graph of the specific detection of 20 amino acids by the exemplary tryptophan optical sensor described in Example 8.

The reactivity of 30 proteins such as purified 31ft-263/266-cpYFP-T259F with 20 amino acids was detected, and the results showed that the proteins had good specificity, as shown in FIG. 11.

Example 9

Subcellular Organelle Localization and Performance Within Subcellular Organelles of Optical Sensors In this example, different localization signal peptides were used to fuse to the optical sensor 31ft-263/266-cpYFP-T259F to localize the optical sensor at different organelles.

Figure 12:
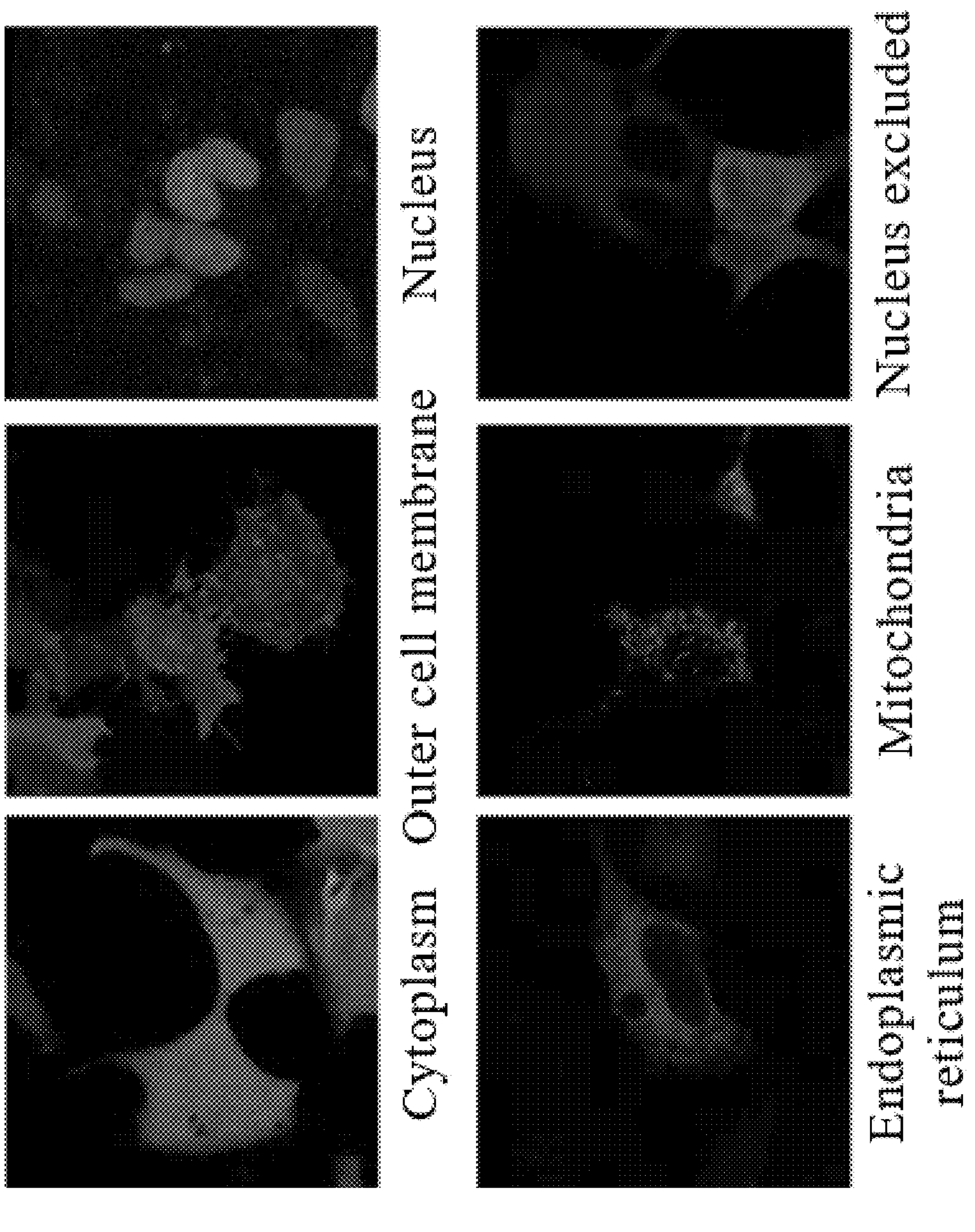
FIG. 12 is a photograph of the subcellular organelle localization of the exemplary tryptophan optical sensor in mammalian cells as described in Example 9.

HeLa cells were transfected for 36 hours with optical sensor plasmids fused with different localization signal peptides, rinsed with PBS, placed in HMS solution, and subjected to fluorescence detection under the FITC channel under an inverted fluorescence microscope. The results are shown in FIG. 12. Tryptophan optical sensors can be localized to subcellular organelles including cytoplasm, outer membrane, nucleus, endoplasmic reticulum, mitochondria and nuclear exclusion by fusing with different specific localization signal peptides. Fluorescence was present in different subcellular structures, and the distribution and intensity of fluorescence varied.

Example 10

Figure 13:
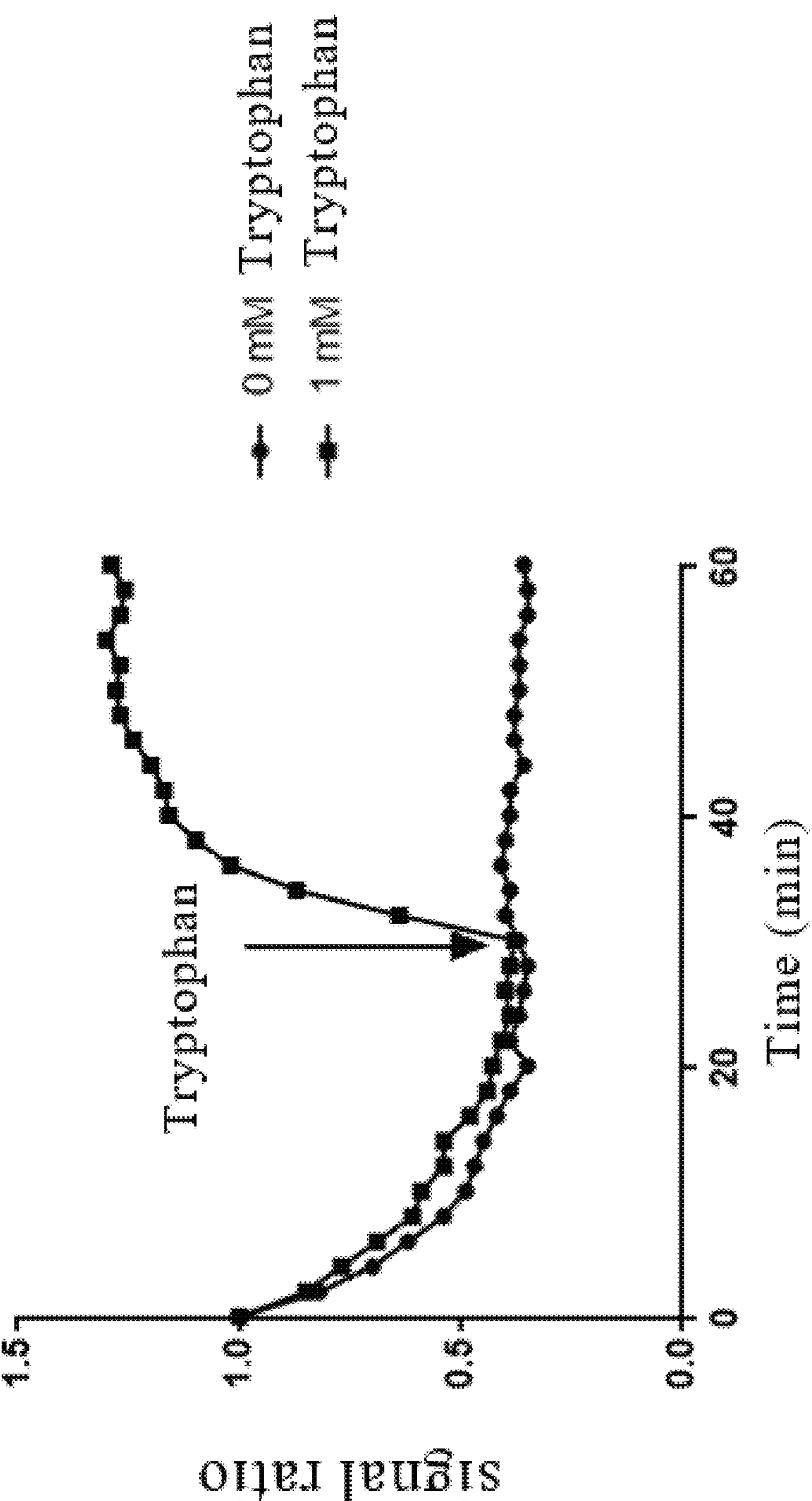
FIG. 13 is a schematic diagram of the dynamic monitoring of cytoplasmic tryptophan concentration in mammalian cells with an exemplary tryptophan optical sensor as described in Example 10.

Dynamic Monitoring of Tryptophan Transmembrane Transport 36 hours after transfection of HeLa cells with plasmids encoding cytosolically expressed optical sensor, cells were rinsed using PBS, placed in HBSS solution, and then changes in the ratio of the fluorescence intensity at 528 nm emission excited at 420 nm to that at 528 nm emission excited at 485 nm were detected over 30 min. The results are shown in FIG. 13. Add 1 mM tryptophan and continue the assay for 30 minutes. The 485/420 ratio of the samples gradually increased after adding tryptophan, and the highest ratio could reach 1.3 times the initial value, while the 485/420 ratio of the control group without tryptophan was 0.38 and remained unchanged.

Example 11

Optical Sensor-Based High-Throughput Compound Screening in Living Cells

In this example, we used HeLa cells expressing 31ft-263/266-cpYFP-T259F in the cytoplasm for high-throughput compound screening.

Figure 14:
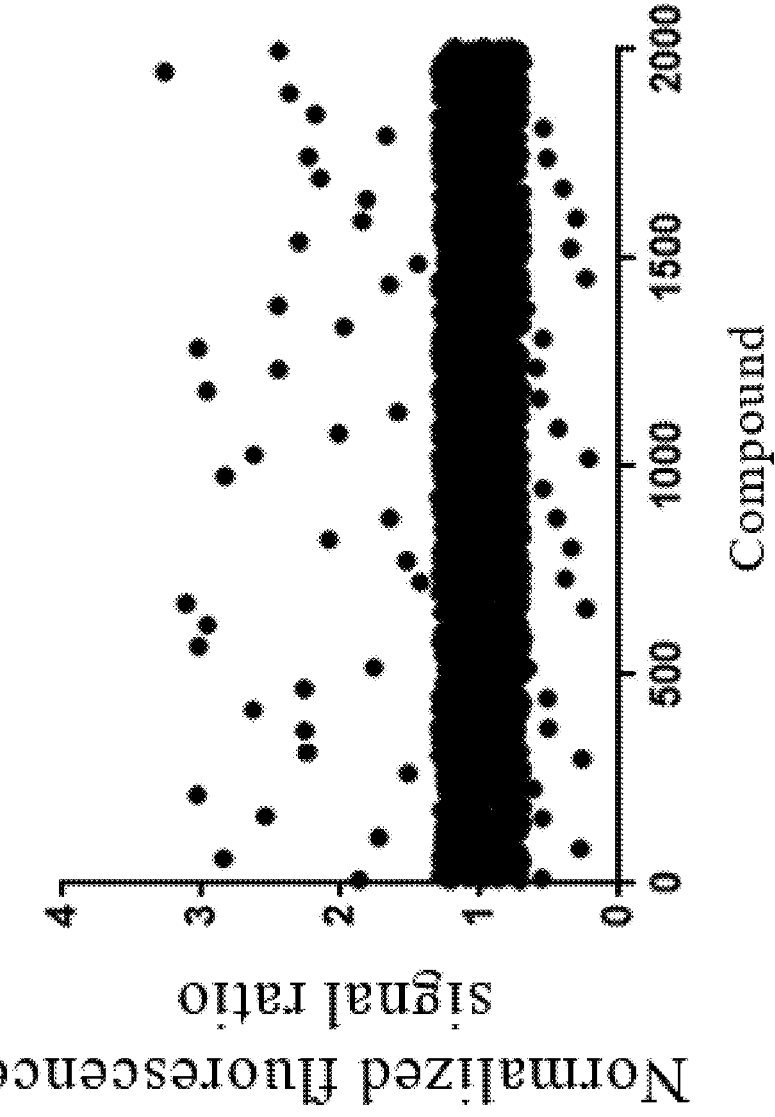
FIG. 14 is a dot plot of high-throughput compound screening in living cells by the exemplary tryptophan optical sensor as described in Example 11.

Transfected HeLa cells were rinsed with PBS, treated in HMS solution (without tryptophan) for 1 hr, and then treated with 10 μM of compound for 1 hr. Tryptophan was added to each sample. Changes in the ratio of fluorescence intensity at 528 nm emission excited at 420 nm to that of 528 nm emission excited at 485 nm were recorded using a microplate reader Samples not treated with any compound were used as controls for normalization The results are shown in FIG. 14. Of the 2000 compounds used, the vast majority had minimal effect on the entry of tryptophan into cells. Twelve compounds were able to increase the cellular uptake of tryptophan, and other 9 compounds were able to decrease the cellular uptake of tryptophan significantly.

Example 12

Quantitative Detection of Tryptophan in Blood with Optical Sensors

In this example, purified 31ft-263/265-cpYFP-F202W was used to analyze tryptophan in blood supernatants of mice and humans.

Figure 15:
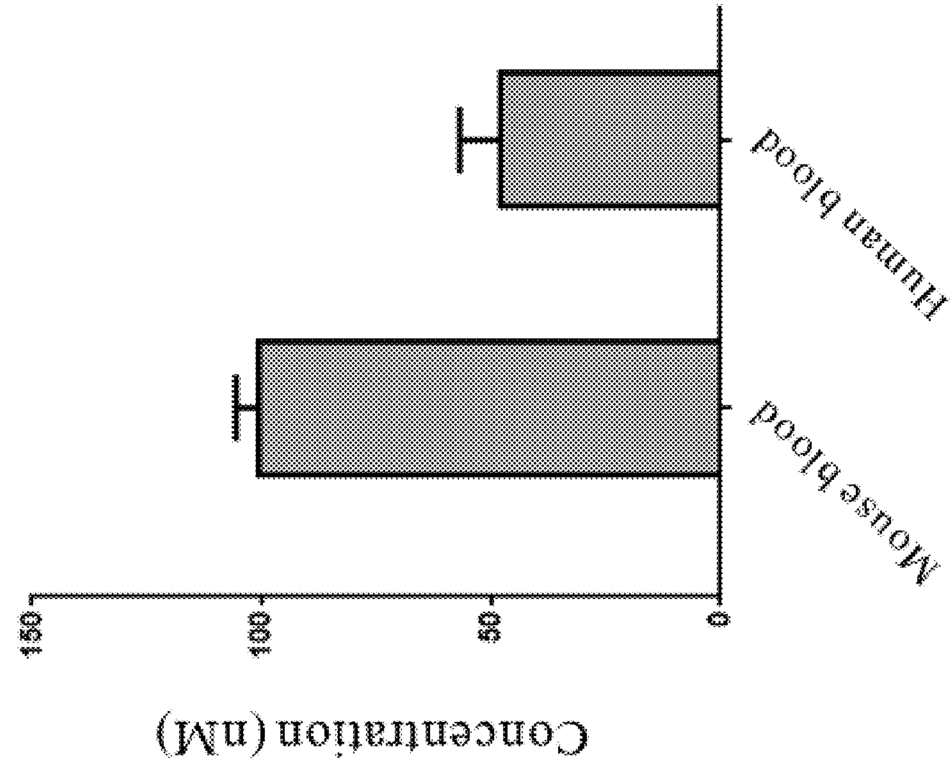
FIG. 15 is a bar graph of the quantification of tryptophan in mouse and human blood by the exemplary tryptophan optical sensor as described in Example 12.

After 10 min of treatment by mixing 31ft-263/265-cpYFP-F202W with diluted blood supernatant, the ratio of fluorescence intensity at 528 nm emission excited at 420 nm to that at 528 nm emission excited at 485 nm was detected using a microplate reader. The results are shown in FIG. 15. The tryptophan content were around 100 μM in mouse blood and around 48 μM in human blood.

It can be seen from the above examples that the tryptophan fluorescent sensor provided by the present invention has relatively small protein molecular weight and was prone to maturation, had large dynamic change in fluorescence, good specificity, and ability to be expressed in cells by gene manipulation methods, which could locate, quantitatively detect tryptophan in real time inside and outside cells; and enables high-throughput compound screening.

OTHER EMBODIMENTS

This specification describes a number of embodiments. It should be understood, however, that various modifications that those skilled in the art will come to know from reading this specification without departing from the spirit and scope of the invention should also be included within the scope of the appended claims.

The invention claimed is:

1. An optical sensor comprising: a tryptophan-sensitive polypeptide having tryptophan-binding function and an optically active polypeptide, wherein the tryptophan-sensitive polypeptide has a sequence having at least 80% sequence identity with SEQ ID NO: 1 and having tryptophan-binding function, and wherein the optically active polypeptide is a fluorescent protein or a functional variant thereof and is operably fused into the tryptophan-sensitive polypeptide at one or more positions of the tryptophan-sensitive polypeptide selected from the group consisting of: 263/265, 263/266, 263/267 and 263/268, wherein the optical sensor responds to tryptophan with the change in optical property.

2. A nucleic acid sequence encoding the optical sensor of claim 1.

3. A nucleic acid construct comprising the nucleic acid sequence according to claim 2.

4. A host cell, wherein the host cell comprises the nucleic acid construct of claim 3 that expresses the optical sensor of claim 1.

5. A method for producing the optical sensor according to claim 1, comprising: culturing the host cell according to claim 4, and separating the expressed optical sensor from the culture.

6. A detection kit comprising (1) the optical sensor according to claim 1;

(2) the nucleic acid sequence according to claim 2 encoding the optical sensor of claim 1;

(3) the nucleic acid construct of claim 3 comprising the nucleic acid sequence of claim 5; or (4) the host cell according to claim 4 comprising the nucleic acid construct of claim 3 that expresses the optical sensor of claim 1.

7. The optical sensor of claim 1, wherein the tryptophan-sensitive polypeptide comprises a mutation at a position selected from the group consisting of: H13, T71, L84, D93, K105, N117, T130, V170, V192, F202, K214, Y217, K255, T259 and I283.

8. The optical sensor of claim 7, wherein the mutation is selected from the group consisting of: H13F, H13W, T71F, T71W, L84F, L84W, D93F, D93W, K105F, K105W, N117F, N117W, T130F, T130W, V170F, V170W, V192F, V192W, F202W, K214F, K214W, Y217F, Y217W, K255F, K255W, T259F, T259W, I283F and I283W.

9. The optical sensor of claim 8, wherein the mutation is selected from the group consisting of: H13F, L84F, L84W, D93F, D93W, K105F, K105W, N117F, N117W, V170F, V170W, V192F, F202W, K214F, K214W, Y217F, Y217W, K255F, K255W, T259F, T259W, I283F and I283W.

* * * * *

SEQUENCE LISTING

```
<160> NUMBER OF SEQ ID NOS: 40

<210> SEQ ID NO 1
<211> LENGTH: 295
<212> TYPE: PRT
<213> ORGANISM: Streptococcus pneumoniae

<400> SEQUENCE: 1

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60
```

```
Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Phe Ser Thr Gly Lys Ser Val Ile Asn
            260                 265                 270

Lys Lys Ile Ala Gln Glu Leu Gly Ile Thr Ile Pro Glu Ser Val Leu
        275                 280                 285

Lys Glu Ala Gly Gln Val Ile
    290                 295


<210> SEQ ID NO 2
<211> LENGTH: 246
<212> TYPE: PRT
<213> ORGANISM: Artificial Sequence
<220> FEATURE:
<223> OTHER INFORMATION: cpYFP

<400> SEQUENCE: 2

Tyr Asn Ser Asp Asn Val Tyr Ile Met Ala Asp Lys Gln Lys Asn Gly
1               5                   10                  15

Ile Lys Ala Asn Phe Lys Ile Arg His Asn Val Glu Asp Gly Ser Val
            20                  25                  30

Gln Leu Ala Asp His Tyr Gln Gln Asn Thr Pro Ile Gly Asp Gly Pro
        35                  40                  45

Val Leu Leu Pro Asp Asn His Tyr Leu Ser Phe Gln Ser Val Leu Ser
    50                  55                  60

Lys Asp Pro Asn Glu Lys Arg Asp His Met Val Leu Leu Glu Phe Val
65                  70                  75                  80

Thr Ala Ala Gly Ile Thr Leu Gly Met Asp Glu Leu Tyr Asn Val Asp
                85                  90                  95

Gly Gly Ser Gly Gly Thr Gly Ser Lys Gly Glu Glu Leu Phe Thr Gly
            100                 105                 110

Val Val Pro Ile Leu Val Glu Leu Asp Gly Asp Val Asn Gly His Lys
        115                 120                 125
```

```
Phe Ser Val Ser Gly Glu Gly Glu Gly Asp Ala Thr Tyr Gly Lys Leu
    130                 135                 140

Thr Leu Lys Leu Ile Cys Thr Thr Gly Lys Leu Pro Val Pro Trp Pro
145                 150                 155                 160

Thr Leu Val Thr Thr Leu Gly Tyr Gly Leu Lys Cys Phe Ala Arg Tyr
                165                 170                 175

Pro Asp His Met Lys Gln His Asp Phe Phe Lys Ser Ala Met Pro Glu
            180                 185                 190

Gly Tyr Val Gln Glu Arg Thr Ile Phe Phe Lys Asp Asp Gly Asn Tyr
        195                 200                 205

Lys Thr Arg Ala Glu Val Lys Phe Glu Gly Asp Thr Leu Val Asn Arg
    210                 215                 220

Ile Glu Leu Lys Gly Ile Asp Phe Lys Glu Asp Gly Asn Ile Leu Gly
225                 230                 235                 240

His Lys Leu Glu Tyr Asn
                245


<210> SEQ ID NO 3
<211> LENGTH: 241
<212> TYPE: PRT
<213> ORGANISM: Artificial Sequence
<220> FEATURE:
<223> OTHER INFORMATION: cpGFP

<400> SEQUENCE: 3

Asn Val Tyr Ile Lys Ala Asp Lys Gln Lys Asn Gly Ile Lys Ala Asn
1               5                   10                  15

Phe Lys Ile Arg His Asn Ile Glu Asp Gly Gly Val Gln Leu Ala Tyr
            20                  25                  30

His Tyr Gln Gln Asn Thr Pro Ile Gly Asp Gly Pro Val Leu Leu Pro
        35                  40                  45

Asp Asn His Tyr Leu Ser Val Gln Ser Ile Leu Ser Lys Asp Pro Asn
    50                  55                  60

Glu Lys Arg Asp His Met Val Leu Leu Glu Phe Val Thr Ala Ala Gly
65                  70                  75                  80

Ile Thr Leu Gly Met Asp Glu Leu Tyr Lys Gly Gly Thr Gly Gly Ser
                85                  90                  95

Met Val Ser Lys Gly Glu Glu Leu Phe Thr Gly Val Val Pro Ile Gln
            100                 105                 110

Val Glu Leu Asp Gly Asp Val Asn Gly His Lys Phe Ser Val Ser Gly
        115                 120                 125

Glu Gly Glu Gly Asp Ala Thr Tyr Gly Lys Leu Thr Leu Lys Phe Ile
    130                 135                 140

Cys Thr Thr Gly Lys Leu Pro Val Pro Trp Pro Thr Leu Val Thr Thr
145                 150                 155                 160

Leu Thr Tyr Gly Val Gln Cys Phe Ser Arg Tyr Pro Asp His Met Lys
                165                 170                 175

Gln His Asp Phe Phe Lys Ser Ala Met Pro Glu Gly Tyr Ile Gln Glu
            180                 185                 190

Arg Thr Ile Phe Phe Lys Asp Asp Gly Asn Tyr Lys Thr Arg Ala Glu
        195                 200                 205

Val Lys Phe Glu Gly Asp Thr Leu Val Asn Arg Ile Glu Leu Lys Gly
    210                 215                 220

Ile Asp Phe Lys Glu Asp Gly Asn Ile Leu Gly His Lys Leu Glu Tyr
225                 230                 235                 240
```

Asn

<210> SEQ ID NO 4
<211> LENGTH: 243
<212> TYPE: PRT
<213> ORGANISM: Artificial Sequence
<220> FEATURE:
<223> OTHER INFORMATION: cpBFP

<400> SEQUENCE: 4

Asn Val Tyr Ile Lys Ala Asp Lys Gln Lys Asn Gly Ile Lys Ala Asn
1 5 10 15

Phe Lys Ile Arg His Asn Ile Glu Gly Gly Gly Val Gln Leu Ala Tyr
20 25 30

His Tyr Gln Gln Asn Thr Pro Ile Gly Asp Gly Pro Val Leu Leu Pro
35 40 45

Asp Asn His Tyr Leu Ser Val Gln Ser Ile Leu Ser Lys Asp Pro Asn
50 55 60

Glu Lys Arg Asp His Met Val Leu Leu Glu Phe Val Thr Ala Ala Gly
65 70 75 80

Ile Thr Leu Gly Met Asp Glu Leu Tyr Lys Gly Gly Thr Gly Gly Ser
85 90 95

Glu Ser Met Val Ser Lys Gly Glu Glu Leu Phe Thr Gly Val Val Pro
100 105 110

Ile Gln Val Glu Leu Asp Gly Asp Val Asn Gly His Lys Phe Ser Val
115 120 125

Ser Gly Glu Gly Glu Gly Asp Ala Thr Tyr Gly Lys Leu Thr Leu Lys
130 135 140

Phe Ile Cys Thr Thr Gly Lys Leu Pro Val Pro Trp Pro Thr Leu Val
145 150 155 160

Thr Thr Leu Ser His Gly Val Gln Cys Phe Ser Arg Tyr Pro Asp His
165 170 175

Met Lys Gln His Asp Phe Phe Lys Ser Ala Met Pro Gly Gly Tyr Ile
180 185 190

Gln Glu Arg Thr Ile Phe Phe Lys Asp Asp Gly Asn Tyr Lys Thr Arg
195 200 205

Ala Glu Val Lys Phe Glu Gly Asp Thr Leu Val Asn Arg Ile Glu Leu
210 215 220

Lys Gly Ile Asp Phe Lys Glu Asp Gly Asn Ile Leu Gly His Lys Leu
225 230 235 240

Glu Tyr Asn

<210> SEQ ID NO 5
<211> LENGTH: 242
<212> TYPE: PRT
<213> ORGANISM: Artificial Sequence
<220> FEATURE:
<223> OTHER INFORMATION: cpmApple

<400> SEQUENCE: 5

Val Ser Glu Arg Met Tyr Pro Glu Asp Gly Ala Leu Lys Ser Glu Ile
1 5 10 15

Lys Lys Gly Leu Arg Leu Lys Asp Gly Gly His Tyr Ala Ala Glu Val
20 25 30

Lys Thr Thr Tyr Lys Ala Lys Lys Pro Val Gln Leu Pro Gly Ala Tyr
35 40 45

```
Ile Val Asp Ile Lys Leu Asp Ile Val Ser His Asn Glu Asp Tyr Thr
    50                  55                  60

Ile Val Glu Gln Cys Glu Arg Ala Glu Gly Arg His Ser Thr Gly Gly
65                  70                  75                  80

Met Asp Glu Leu Tyr Lys Gly Gly Thr Gly Gly Ser Leu Val Ser Lys
                85                  90                  95

Gly Glu Glu Asp Asn Met Ala Ile Ile Lys Glu Phe Met Arg Phe Lys
            100                 105                 110

Val His Met Glu Gly Ser Val Asn Gly His Glu Phe Glu Ile Glu Gly
        115                 120                 125

Glu Gly Glu Gly Arg Pro Tyr Glu Ala Phe Gln Thr Ala Lys Leu Lys
    130                 135                 140

Val Thr Lys Gly Gly Pro Leu Pro Phe Ala Trp Asp Ile Leu Ser Pro
145                 150                 155                 160

Gln Phe Met Tyr Gly Ser Lys Ala Tyr Ile Lys His Pro Ala Asp Ile
                165                 170                 175

Pro Asp Tyr Phe Lys Leu Ser Phe Pro Glu Gly Phe Arg Trp Glu Arg
            180                 185                 190

Val Met Asn Phe Glu Asp Gly Gly Ile Ile His Val Asn Gln Asp Ser
        195                 200                 205

Ser Leu Gln Asp Gly Val Phe Ile Tyr Lys Val Lys Leu Arg Gly Thr
    210                 215                 220

Asn Phe Pro Pro Asp Gly Pro Val Met Gln Lys Lys Thr Met Gly Trp
225                 230                 235                 240

Glu Ala


<210> SEQ ID NO 6
<211> LENGTH: 540
<212> TYPE: PRT
<213> ORGANISM: Artificial Sequence
<220> FEATURE:
<223> OTHER INFORMATION: sensor

<400> SEQUENCE: 6

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
```

```
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 7
<211> LENGTH: 539
<212> TYPE: PRT
<213> ORGANISM: Artificial Sequence
<220> FEATURE:
<223> OTHER INFORMATION: sensor
```

<400> SEQUENCE: 7

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415
```

```
Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535
```

<210> SEQ ID NO 8
<211> LENGTH: 538
<212> TYPE: PRT
<213> ORGANISM: Artificial Sequence
<220> FEATURE:
<223> OTHER INFORMATION: sensor

<400> SEQUENCE: 8

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240
```

```
Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535


<210> SEQ ID NO 9
<211> LENGTH: 537
<212> TYPE: PRT
<213> ORGANISM: Artificial Sequence
<220> FEATURE:
<223> OTHER INFORMATION: sensor

<400> SEQUENCE: 9

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60
```

-continued

```
Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480
```

```
Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Lys Ser Val
            500                 505                 510

Ile Asn Lys Lys Ile Ala Gln Glu Leu Gly Ile Thr Ile Pro Glu Ser
        515                 520                 525

Val Leu Lys Glu Ala Gly Gln Val Ile
    530                 535


<210> SEQ ID NO 10
<211> LENGTH: 540
<212> TYPE: PRT
<213> ORGANISM: Artificial Sequence
<220> FEATURE:
<223> OTHER INFORMATION: sensor

<400> SEQUENCE: 10

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Phe Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300
```

```
Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 11
<211> LENGTH: 540
<212> TYPE: PRT
<213> ORGANISM: Artificial Sequence
<220> FEATURE:
<223> OTHER INFORMATION: sensor

<400> SEQUENCE: 11

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Phe Pro Gly Gly Asn Val Thr Gly
            100                 105                 110

Val Ser Asp His Asn Pro Ala Gln Gln Gln Val Glu Leu Ile Lys Ala
        115                 120                 125
```

-continued

```
Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540
```

<210> SEQ ID NO 12
<211> LENGTH: 540
<212> TYPE: PRT
<213> ORGANISM: Artificial Sequence
<220> FEATURE:
<223> OTHER INFORMATION: sensor

<400> SEQUENCE: 12

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Trp Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
```

```
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 13
<211> LENGTH: 540
<212> TYPE: PRT
<213> ORGANISM: Artificial Sequence
<220> FEATURE:
<223> OTHER INFORMATION: sensor

<400> SEQUENCE: 13

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
```

```
        195                 200                 205

Asn Gln Ser Ser Lys Phe Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 14
<211> LENGTH: 540
<212> TYPE: PRT
<213> ORGANISM: Artificial Sequence
<220> FEATURE:
<223> OTHER INFORMATION: sensor

<400> SEQUENCE: 14

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
```

```
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Trp Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445
```

```
Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 15
<211> LENGTH: 540
<212> TYPE: PRT
<213> ORGANISM: Artificial Sequence
<220> FEATURE:
<223> OTHER INFORMATION: sensor

<400> SEQUENCE: 15

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Phe Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270
```

```
Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 16
<211> LENGTH: 540
<212> TYPE: PRT
<213> ORGANISM: Artificial Sequence
<220> FEATURE:
<223> OTHER INFORMATION: sensor

<400> SEQUENCE: 16

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95
```

-continued

```
Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Trp Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510
```

```
Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 17
<211> LENGTH: 540
<212> TYPE: PRT
<213> ORGANISM: Artificial Sequence
<220> FEATURE:
<223> OTHER INFORMATION: sensor

<400> SEQUENCE: 17

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Phe Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335
```

```
Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 18
<211> LENGTH: 540
<212> TYPE: PRT
<213> ORGANISM: Artificial Sequence
<220> FEATURE:
<223> OTHER INFORMATION: sensor

<400> SEQUENCE: 18

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160
```

```
Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Trp Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540
```

```
<210> SEQ ID NO 19
<211> LENGTH: 540
<212> TYPE: PRT
<213> ORGANISM: Artificial Sequence
<220> FEATURE:
<223> OTHER INFORMATION: sensor
```

<400> SEQUENCE: 19

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Phe Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
```

```
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 20
<211> LENGTH: 540
<212> TYPE: PRT
<213> ORGANISM: Artificial Sequence
<220> FEATURE:
<223> OTHER INFORMATION: sensor

<400> SEQUENCE: 20

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
```

```
225                 230                 235                 240

Val Ala Thr Gly Lys Met Ile Val Gln Val Leu Lys Gly Ala Lys Pro
                245                 250                 255

Ala Asp Trp Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Ile
        515                 520                 525

Pro Glu Ser Val Leu Lys Glu Ala Gly Gln Val Ile
    530                 535                 540


<210> SEQ ID NO 21
<211> LENGTH: 540
<212> TYPE: PRT
<213> ORGANISM: Artificial Sequence
<220> FEATURE:
<223> OTHER INFORMATION: sensor

<400> SEQUENCE: 21

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
```

-continued

```
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480
```

```
Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Ser Thr Gly
            500                 505                 510

Lys Ser Val Ile Asn Lys Lys Ile Ala Gln Glu Leu Gly Ile Thr Phe
        515                 520                 525

Pro Glu Ser Val Leu Lys Glu Ala Gly Gln Val Ile
    530                 535                 540


<210> SEQ ID NO 22
<211> LENGTH: 540
<212> TYPE: PRT
<213> ORGANISM: Artificial Sequence
<220> FEATURE:
<223> OTHER INFORMATION: sensor

<400> SEQUENCE: 22

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300
```

Thr Pro Ile Gly Asp Gly Pro Val Leu Leu Pro Asp Asn His Tyr Leu
305 310 315 320

Ser Phe Gln Ser Val Leu Ser Lys Asp Pro Asn Glu Lys Arg Asp His
325 330 335

Met Val Leu Leu Glu Phe Val Thr Ala Ala Gly Ile Thr Leu Gly Met
340 345 350

Asp Glu Leu Tyr Asn Val Asp Gly Gly Ser Gly Gly Thr Gly Ser Lys
355 360 365

Gly Glu Glu Leu Phe Thr Gly Val Val Pro Ile Leu Val Glu Leu Asp
370 375 380

Gly Asp Val Asn Gly His Lys Phe Ser Val Ser Gly Glu Gly Glu Gly
385 390 395 400

Asp Ala Thr Tyr Gly Lys Leu Thr Leu Lys Leu Ile Cys Thr Thr Gly
405 410 415

Lys Leu Pro Val Pro Trp Pro Thr Leu Val Thr Thr Leu Gly Tyr Gly
420 425 430

Leu Lys Cys Phe Ala Arg Tyr Pro Asp His Met Lys Gln His Asp Phe
435 440 445

Phe Lys Ser Ala Met Pro Glu Gly Tyr Val Gln Glu Arg Thr Ile Phe
450 455 460

Phe Lys Asp Asp Gly Asn Tyr Lys Thr Arg Ala Glu Val Lys Phe Glu
465 470 475 480

Gly Asp Thr Leu Val Asn Arg Ile Glu Leu Lys Gly Ile Gly Phe Lys
485 490 495

Glu Asp Gly Asn Ile Leu Gly His Lys Leu Glu Tyr Asn Ser Thr Gly
500 505 510

Lys Ser Val Ile Asn Lys Lys Ile Ala Gln Glu Leu Gly Ile Thr Trp
515 520 525

Pro Glu Ser Val Leu Lys Glu Ala Gly Gln Val Ile
530 535 540

<210> SEQ ID NO 23
<211> LENGTH: 539
<212> TYPE: PRT
<213> ORGANISM: Artificial Sequence
<220> FEATURE:
<223> OTHER INFORMATION: sensor

<400> SEQUENCE: 23

Ser Asn Ala Lys Ile Gly Val Leu Gln Phe Val Ser His Pro Ser Leu
1 5 10 15

Asp Leu Ile Tyr Lys Gly Ile Gln Asp Gly Leu Ala Glu Glu Gly Tyr
20 25 30

Lys Asp Asp Gln Val Lys Ile Asp Phe Met Asn Ser Glu Gly Asp Gln
35 40 45

Ser Lys Val Ala Thr Met Ser Lys Gln Leu Val Ala Asn Gly Asn Asp
50 55 60

Leu Val Val Gly Ile Ala Thr Pro Ala Ala Gln Gly Leu Ala Ser Ala
65 70 75 80

Thr Lys Asp Phe Pro Val Ile Met Ala Ala Ile Thr Asp Pro Ile Gly
85 90 95

Ala Asn Leu Val Lys Asp Leu Lys Lys Pro Gly Gly Asn Val Thr Gly
100 105 110

Val Ser Asp His Asn Pro Ala Gln Gln Gln Val Glu Leu Ile Lys Ala
115 120 125

```
Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535
```

<210> SEQ ID NO 24
<211> LENGTH: 539
<212> TYPE: PRT
<213> ORGANISM: Artificial Sequence
<220> FEATURE:
<223> OTHER INFORMATION: sensor

<400> SEQUENCE: 24

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Phe Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365
```

```
Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535
```

<210> SEQ ID NO 25
<211> LENGTH: 539
<212> TYPE: PRT
<213> ORGANISM: Artificial Sequence
<220> FEATURE:
<223> OTHER INFORMATION: sensor

<400> SEQUENCE: 25

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Trp Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190
```

```
Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535


<210> SEQ ID NO 26
<211> LENGTH: 539
<212> TYPE: PRT
<213> ORGANISM: Artificial Sequence
<220> FEATURE:
<223> OTHER INFORMATION: sensor

<400> SEQUENCE: 26

Ser Asn Ala Lys Ile Gly Val Leu Gln Phe Val Ser His Pro Ser Leu
1               5                   10                  15
```

```
Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Trp Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
```

```
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535


<210> SEQ ID NO 27
<211> LENGTH: 539
<212> TYPE: PRT
<213> ORGANISM: Artificial Sequence
<220> FEATURE:
<223> OTHER INFORMATION: sensor

<400> SEQUENCE: 27

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Phe Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
```

```
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535


<210> SEQ ID NO 28
<211> LENGTH: 539
<212> TYPE: PRT
<213> ORGANISM: Artificial Sequence
<220> FEATURE:
<223> OTHER INFORMATION: sensor

<400> SEQUENCE: 28

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
```

-continued

```
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Trp Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510
```

```
Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535


<210> SEQ ID NO 29
<211> LENGTH: 539
<212> TYPE: PRT
<213> ORGANISM: Artificial Sequence
<220> FEATURE:
<223> OTHER INFORMATION: sensor

<400> SEQUENCE: 29

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Phe Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335
```

```
Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535


<210> SEQ ID NO 30
<211> LENGTH: 539
<212> TYPE: PRT
<213> ORGANISM: Artificial Sequence
<220> FEATURE:
<223> OTHER INFORMATION: sensor

<400> SEQUENCE: 30

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160
```

```
Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Trp Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535
```

<210> SEQ ID NO 31
<211> LENGTH: 539
<212> TYPE: PRT
<213> ORGANISM: Artificial Sequence
<220> FEATURE:

<223> OTHER INFORMATION: sensor

<400> SEQUENCE: 31

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Phe Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400
```

```
Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535
```

<210> SEQ ID NO 32
<211> LENGTH: 539
<212> TYPE: PRT
<213> ORGANISM: Artificial Sequence
<220> FEATURE:
<223> OTHER INFORMATION: sensor

<400> SEQUENCE: 32

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220
```

```
Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Trp Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Ile Pro
        515                 520                 525

Glu Ser Val Leu Lys Glu Ala Gly Gln Val Ile
    530                 535


<210> SEQ ID NO 33
<211> LENGTH: 539
<212> TYPE: PRT
<213> ORGANISM: Artificial Sequence
<220> FEATURE:
<223> OTHER INFORMATION: sensor

<400> SEQUENCE: 33

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45
```

```
Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
```

```
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Thr Gly Lys
            500                 505                 510

Ser Val Ile Asn Lys Lys Ile Ala Gln Glu Leu Gly Ile Thr Phe Pro
        515                 520                 525

Glu Ser Val Leu Lys Glu Ala Gly Gln Val Ile
    530                 535


<210> SEQ ID NO 34
<211> LENGTH: 538
<212> TYPE: PRT
<213> ORGANISM: Artificial Sequence
<220> FEATURE:
<223> OTHER INFORMATION: sensor

<400> SEQUENCE: 34

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Phe Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
```

```
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535


<210> SEQ ID NO 35
<211> LENGTH: 538
<212> TYPE: PRT
<213> ORGANISM: Artificial Sequence
<220> FEATURE:
<223> OTHER INFORMATION: sensor

<400> SEQUENCE: 35

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Phe Pro Gly Gly Asn Val Thr Gly
            100                 105                 110

Val Ser Asp His Asn Pro Ala Gln Gln Gln Val Glu Leu Ile Lys Ala
```

```
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535
```

<210> SEQ ID NO 36
<211> LENGTH: 538
<212> TYPE: PRT
<213> ORGANISM: Artificial Sequence
<220> FEATURE:
<223> OTHER INFORMATION: sensor

<400> SEQUENCE: 36

```
Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Trp Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365
```

```
Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535


<210> SEQ ID NO 37
<211> LENGTH: 538
<212> TYPE: PRT
<213> ORGANISM: Artificial Sequence
<220> FEATURE:
<223> OTHER INFORMATION: sensor

<400> SEQUENCE: 37

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190
```

```
Pro Ile Asp Asn Thr Ile Ala Ser Gly Trp Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535
```

<210> SEQ ID NO 38
<211> LENGTH: 538
<212> TYPE: PRT
<213> ORGANISM: Artificial Sequence
<220> FEATURE:
<223> OTHER INFORMATION: sensor

<400> SEQUENCE: 38

```
Ser Asn Ala Lys Ile Gly Val Leu Gln Phe Val Ser His Pro Ser Leu
1               5                   10                  15
```

```
Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Phe Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255

Ala Asp Thr Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430
```

```
Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535


<210> SEQ ID NO 39
<211> LENGTH: 538
<212> TYPE: PRT
<213> ORGANISM: Artificial Sequence
<220> FEATURE:
<223> OTHER INFORMATION: sensor

<400> SEQUENCE: 39

Ser Asn Ala Lys Ile Gly Val Leu Gln Phe Val Ser His Pro Ser Leu
1               5                   10                  15

Asp Leu Ile Tyr Lys Gly Ile Gln Asp Gly Leu Ala Glu Glu Gly Tyr
            20                  25                  30

Lys Asp Asp Gln Val Lys Ile Asp Phe Met Asn Ser Glu Gly Asp Gln
        35                  40                  45

Ser Lys Val Ala Thr Met Ser Lys Gln Leu Val Ala Asn Gly Asn Asp
    50                  55                  60

Leu Val Val Gly Ile Ala Thr Pro Ala Ala Gln Gly Leu Ala Ser Ala
65                  70                  75                  80

Thr Lys Asp Leu Pro Val Ile Met Ala Ala Ile Thr Asp Pro Ile Gly
                85                  90                  95

Ala Asn Leu Val Lys Asp Leu Lys Lys Pro Gly Gly Asn Val Thr Gly
            100                 105                 110

Val Ser Asp His Asn Pro Ala Gln Gln Gln Val Glu Leu Ile Lys Ala
        115                 120                 125

Leu Thr Pro Asn Val Lys Thr Ile Gly Ala Leu Tyr Ser Ser Ser Glu
    130                 135                 140

Asp Asn Ser Lys Thr Gln Val Glu Glu Phe Lys Ala Tyr Ala Glu Lys
145                 150                 155                 160

Ala Gly Leu Thr Val Glu Thr Phe Ala Val Pro Ser Thr Asn Glu Ile
                165                 170                 175

Ala Ser Thr Val Thr Val Met Thr Ser Lys Val Asp Ala Ile Trp Val
            180                 185                 190

Pro Ile Asp Asn Thr Ile Ala Ser Gly Phe Pro Thr Val Val Ser Ser
        195                 200                 205

Asn Gln Ser Ser Lys Lys Pro Ile Tyr Pro Ser Ala Thr Ala Met Val
    210                 215                 220

Glu Val Gly Gly Leu Ala Ser Val Val Ile Asp Gln His Asp Leu Gly
225                 230                 235                 240

Val Ala Thr Gly Lys Met Ile Val Gln Val Leu Lys Gly Ala Lys Pro
                245                 250                 255
```

```
Ala Asp Phe Pro Val Asn Val Tyr Asn Ser Asp Asn Val Tyr Ile Met
            260                 265                 270

Ala Asp Lys Gln Lys Asn Gly Ile Lys Ala Asn Phe Lys Ile Arg His
        275                 280                 285

Asn Val Glu Asp Gly Ser Val Gln Leu Ala Asp His Tyr Gln Gln Asn
    290                 295                 300

Thr Pro Ile Gly Asp Gly Pro Val Leu Leu Pro Asp Asn His Tyr Leu
305                 310                 315                 320

Ser Phe Gln Ser Val Leu Ser Lys Asp Pro Asn Glu Lys Arg Asp His
                325                 330                 335

Met Val Leu Leu Glu Phe Val Thr Ala Ala Gly Ile Thr Leu Gly Met
            340                 345                 350

Asp Glu Leu Tyr Asn Val Asp Gly Gly Ser Gly Gly Thr Gly Ser Lys
        355                 360                 365

Gly Glu Glu Leu Phe Thr Gly Val Val Pro Ile Leu Val Glu Leu Asp
    370                 375                 380

Gly Asp Val Asn Gly His Lys Phe Ser Val Ser Gly Glu Gly Glu Gly
385                 390                 395                 400

Asp Ala Thr Tyr Gly Lys Leu Thr Leu Lys Leu Ile Cys Thr Thr Gly
                405                 410                 415

Lys Leu Pro Val Pro Trp Pro Thr Leu Val Thr Thr Leu Gly Tyr Gly
            420                 425                 430

Leu Lys Cys Phe Ala Arg Tyr Pro Asp His Met Lys Gln His Asp Phe
        435                 440                 445

Phe Lys Ser Ala Met Pro Glu Gly Tyr Val Gln Glu Arg Thr Ile Phe
    450                 455                 460

Phe Lys Asp Asp Gly Asn Tyr Lys Thr Arg Ala Glu Val Lys Phe Glu
465                 470                 475                 480

Gly Asp Thr Leu Val Asn Arg Ile Glu Leu Lys Gly Ile Gly Phe Lys
                485                 490                 495

Glu Asp Gly Asn Ile Leu Gly His Lys Leu Glu Tyr Asn Gly Lys Ser
            500                 505                 510

Val Ile Asn Lys Lys Ile Ala Gln Glu Leu Gly Ile Thr Ile Pro Glu
        515                 520                 525

Ser Val Leu Lys Glu Ala Gly Gln Val Ile
    530                 535
```

<210> SEQ ID NO 40
<211> LENGTH: 1617
<212> TYPE: DNA
<213> ORGANISM: Artificial Sequence
<220> FEATURE:
<223> OTHER INFORMATION: sensor

<400> SEQUENCE: 40

```
agcaacgcga agattggtgt gctgcaattt gtgagccacc cgagcctgga cctgatttac      60

aaaggtatcc aggacggtct ggctgaagag ggttacaagg atgaccaggt gaaaatcgac     120

ttcatgaaca gcgagggtga ccagagcaag gtggccacca tgagcaaaca gctggtggct     180

aacggtaacg acctggtggt gggtatcgcc accccggccg cgcagggtct ggccagcgcc     240

accaaggacc tgccggtaat tatggcggct atcaccgacc cgattggtgc gaacctggtg     300

aaagacctga aaaagccggg tggcaacgtg accggcgtga gcgaccacaa cccggcccag     360

cagcaggtgg agctgattaa ggcgctgacc ccgaacgtga agaccatcgg tgccctgtat     420

agcagcagcg aagacaacag caagacccag gtggaagagt tcaaggcgta cgctgagaag     480
```

-continued

```
gcgggtctga ccgtggaaac cttcgctgtg ccgagcacca acgagattgc gagcaccgtg    540

accgtgatga ccagcaaagt ggatgctatc tgggtgccga ttgacaacac cattgccagc    600

ggctttccga ccgtggtgag cagcaaccag agcagcaaga aaccgattta cccgagcgcc    660

accgcgatgg tggaagtggg cggtctggcg agcgtggtaa ttgaccagca cgacctgggt    720

gtggcgaccg gcaaaatgat tgtgcaggtg ctgaagggtg cgaaaccggc ggacttcccg    780

gtgaacgtgt acaacagcga caacgtctat atcatggccg acaagcagaa gaacggcatc    840

aaggccaact tcaagatccg ccacaacgtc gaggacggca gcgtgcagct cgccgaccac    900

taccagcaga acacccccat cggcgacggc cccgtgctgc tgcccgacaa ccactacctg    960

agcttccagt ccgtcctgag caaagacccc aacgagaagc gcgatcacat ggtcctgctg   1020

gagttcgtga ccgccgccgg gatcactctc ggcatggacg agctgtacaa cgtggatggc   1080

ggtagcggtg gcaccggcag caagggcgag gagctgttca ccggggtggt gcccatcctg   1140

gtcgagctgg acggcgacgt aaacggccac aagttcagcg tgtccggcga gggcgagggc   1200

gatgccacct acggcaagct gaccctgaag ctgatctgca ccaccggcaa gctgcccgtg   1260

ccctggccca ccctcgtgac caccctcggc tacggcctga agtgcttcgc ccgctacccc   1320

gaccacatga agcagcacga cttcttcaag tccgccatgc ccgaaggcta cgtccaggag   1380

cgcaccatct tcttcaagga cgacggcaac tacaagaccc gcgccgaggt gaagttcgag   1440

ggcgacaccc tggtgaaccg catcgagctg aagggcatcg gcttcaagga ggacggcaac   1500

atcctggggc acaagctgga gtacaacacc ggcaaaagcg tgattaacaa gaaaatcgcg   1560

caggagctgg gcatcaccat tccggaaagc gtgctgaaag aggctggcca ggtaatt      1617
```